United States Patent
Bae et al.

(10) Patent No.: US 11,058,482 B2
(45) Date of Patent: Jul. 13, 2021

(54) MULTI-ELECTRODE RENAL DENERVATION METHOD AND SYSTEM USING INTEGRATED CIRCUIT

(71) Applicant: Korea Advanced Institute of Science and Technology, Dajeon (KR)

(72) Inventors: Hyeon Min Bae, Daejeon (KR); Jae Hyeok Yang, Daejeon (KR); Seo Hyeon Kim, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 617 days.

(21) Appl. No.: 15/757,065

(22) PCT Filed: Aug. 30, 2016

(86) PCT No.: PCT/KR2016/009670
§ 371 (c)(1),
(2) Date: May 16, 2018

(87) PCT Pub. No.: WO2017/039288
PCT Pub. Date: Mar. 9, 2017

(65) Prior Publication Data
US 2018/0256248 A1 Sep. 13, 2018

(30) Foreign Application Priority Data
Sep. 3, 2015 (KR) .......................... 10-2015-0124995

(51) Int. Cl.
*A61B 18/12* (2006.01)
*A61B 18/14* (2006.01)
(Continued)

(52) U.S. Cl.
CPC .......... *A61B 18/1492* (2013.01); *A61B 18/08* (2013.01); *A61B 18/1206* (2013.01);
(Continued)

(58) Field of Classification Search
CPC .......... A61M 25/0074; A61B 18/1206; A61B 18/1233; A61B 18/1492; A61B 18/08;
(Continued)

(56) References Cited

U.S. PATENT DOCUMENTS 6,193,713 B1 * 2/2001 Geistert ............ A61B 18/1206
606/32
6,979,329 B2 * 12/2005 Burnside ............ A61B 18/1492
606/41

(Continued)

OTHER PUBLICATIONS

International Search Report dated Dec. 9, 2016.

*Primary Examiner* — Thomas A Giuliani
(74) *Attorney, Agent, or Firm* — Dinsmore & Shohl LLP; Yongsok Choi, Esq.

(57) ABSTRACT

A multi-electrode renal denervation method and system using an integrated circuit are provided. The multi-electrode renal denervation system presented in the present invention comprises: a power generator transmitting control data for controlling the temperature of a plurality of electrodes; and a catheter in which the plurality of electrodes, which has an integrated circuit embedded therein and is controlled by the control data received from the power generator, are arranged, and the information measured using the integrated circuit is transmitted to the power generator.

17 Claims, 22 Drawing Sheets

(51) Int. Cl.
*A61B 18/08* (2006.01)
*A61B 18/00* (2006.01)
*A61B 5/00* (2006.01)
*A61B 17/00* (2006.01)
*A61M 25/00* (2006.01)

(52) U.S. Cl.
CPC ........ *A61B 18/1233* (2013.01); *A61B 5/6852* (2013.01); *A61B 2017/00084* (2013.01); *A61B 2018/0016* (2013.01); *A61B 2018/00267* (2013.01); *A61B 2018/00404* (2013.01); *A61B 2018/00434* (2013.01); *A61B 2018/00511* (2013.01); *A61B 2018/00714* (2013.01); *A61B 2018/00791* (2013.01); *A61B 2018/00875* (2013.01); *A61M 25/0074* (2013.01)

(58) Field of Classification Search
CPC .......... A61B 2018/00875; A61B 2018/00791; A61B 2018/00714; A61B 2018/00511; A61B 2018/00434; A61B 2018/00404; A61B 2018/00267; A61B 2018/0016; A61B 2018/00636; A61B 2018/00642; A61B 2018/0066; A61B 2018/00666; A61B 5/6852; A61B 2017/00084; A61B 18/00–28; A61B 2018/00005–266
USPC ............ 606/34, 38, 41, 42; 607/98, 99, 102, 607/113, 115, 116
See application file for complete search history.

(56) References Cited

U.S. PATENT DOCUMENTS

| | | | | |
|---|---|---|---|---|
| 2003/0120271 | A1* | 6/2003 | Burnside | A61B 18/1492 606/41 |
| 2010/0168739 | A1* | 7/2010 | Wu | A61B 18/1492 606/41 |
| 2011/0285432 | A1* | 11/2011 | Ozawa | H04L 7/033 327/149 |
| 2012/0116383 | A1* | 5/2012 | Mauch | A61M 25/0147 606/33 |
| 2015/0011843 | A1* | 1/2015 | Toth | A61N 1/36185 600/301 |

* cited by examiner

MULTI-ELECTRODE RENAL DENERVATION METHOD AND SYSTEM USING INTEGRATED CIRCUIT

CROSS-REFERENCE TO RELATED APPLICATIONS

This application is a national phase application of Patent Cooperation Treaty (PCT) international application Serial No. PCT/KR2016/009670, filed on Aug. 30, 2016, which claims priority to Korean Patent Application Serial No. 10-2015-0124995, filed on Sep. 3, 2015. The entire contents of PCT international application Serial No. PCT/KR2016/009670, and Korean Patent Application Serial No. 10-2015-0124995 are hereby incorporated by reference.

FIELD OF THE INVENTION

The present invention relates to a multi-electrode renal denervation method and system using an integrated circuit.

BACKGROUND

Resistant hypertension, which applies to 20% to 30% of all hypertensive patients, refers to a disease in which blood pressure is not controlled below a target level even when three or more types of hypotensors including diuretics are taken. Renal nerve block, which is a representative treatment for resistant hypertension, reduces sympathetic activity and lowers blood pressure by blocking renal nerves that transmit signals to a renin-angiotensin-aldosterone system (RAAS), which is one of important mechanisms involved in blood pressure control. The renal sympathetic nerves are located in subdermal layers of renal arteries, and the renal arteries are the only places where afferent and efferent sympathetic nerves pass together.

A single-electrode system, which uses one electrode for a single procedure usually performed over 6 to 7 points spirally disposed along the inner wall of the artery, has a disadvantage in that it takes a long time to perform the procedure and the risks of side effects and complications of a patient are increased. Further, expertise is required when one electrode is used, because maintaining the electrode at a proper location of a blood vessel wall during the procedure relies on the direct control of a surgeon.

Although a multi-electrode system using multiple electrodes and sensors may shorten a procedure time, the number of wires connected to an external control device is increased in proportion to the number of electrodes. The multiple wires increase the diameter of the catheter 120 that should pass through the blood vessels, so that the procedure cannot be efficiently performed and the yield of a process for manufacturing the apparatus is reduced to increase the cost of the apparatus.

SUMMARY OF THE INVENTION

One object of the present invention is to provide a multi-electrode renal denervation method and system using an integrated circuit to remedy shortcomings that a conventional renal nerve block apparatus takes a long time to perform a procedure and increases the risks of side effects and complications of a patient, and that expertise is required when the procedure is performed using one electrode, because maintaining the electrode at a proper location of a blood vessel wall relies on the direct control of a surgeon. Further, a conventional multi-electrode system using multiple electrodes and sensors may shorten a procedure time, but has a disadvantage in that since the number of wires connected to an external control device is increased in proportion to the number of electrodes, the diameter of a catheter is increased so that the procedure cannot be efficiently performed and the yield of a process for manufacturing an apparatus is reduced to increase the cost of the apparatus. Therefore, there are provided a multi-electrode renal denervation method and system using an integrated circuit to solve the above problems.

According to one aspect of the invention, a proposed multi-electrode renal denervation system comprises: a power generator configured to transmit control data for adjusting temperature of a plurality of electrodes; and a catheter configured to transmit information measured by using an integrated circuit (IC) to the power generator, wherein the plurality of electrodes are disposed in the catheter, and the IC is incorporated in each of the plurality of electrodes and controlled by the control data received from the power generator.

The IC is connected to the power generator using a VDD line for supplying a supply voltage, a GND line, and a data line for data communication. The IC is configured to generate and supply a plurality of voltages required for respective blocks in the IC from the supply voltage supplied through the VDD line using a regulator in the IC.

The data line for data communication is a single wire for sequentially transmitting the control data at predetermined time intervals using a time division communication scheme, thereby enabling bidirectional communication between the power generator and the plurality of ICs.

The control data are in the form of packets transmitted from a micro controller unit (MCU) in the power generator, and the packets have predetermined ID data. The ID data indicate that the control data are transmitted to a specific IC corresponding to a predetermined ID, among the ICs incorporated in the plurality of electrodes.

The specific IC receiving the control data transmits the information measured by using the IC to the power generator in a next time interval, after receiving the control data.

Before the control data are transmitted, frequency and phase synchronization is performed between the MCU in the power generator and the ICs incorporated in the plurality of electrodes.

The IC comprises: a regulator configured to generate and supply a plurality of voltages required for the respective blocks in the IC, using the supply voltage supplied from the power generator through the VDD line; a communication unit configured to receive the control data from the power generator and to digitize information measured by using a temperature sensor and an impedance sensor and transmit the digitized information to the power generator through the single wire; a temperature sensor configured to measure temperature using a temperature proportional current in a bandgap reference circuit; an impedance sensor configured to measure impedance by applying a predetermined current and sensing an absolute value of a voltage change; a shared analog-to-digital converter (ADC) configured to digitize the information measured by the temperature sensor and the impedance sensor; and a heater configured to adjust the temperature by controlling power consumption using the control data received from the power generator.

The heater converts the control data received from the power generator into PWM pulses through a PWM pulse generation circuit, and controls a plurality of MOSFET switches in parallel using the PWM pulses through a driver circuit, thereby controlling power consumption of resistance of the heater so that heat is directly transferred to a blood vessel wall through the electrodes to remove nerves.

The temperature sensor is utilized to increase an amount of a supply current of the heater when the measured temperature is lower than a target temperature, and to decrease the amount of the supply current of the heater when the measured temperature is higher than the target temperature.

The impedance sensor comprises: a digital sine wave generator configured to generate a sine wave voltage using a DDS scheme; an alternating current application circuit configured to convert the generated sine wave voltage into a current and apply an alternating current to the electrodes; a programmable gain amplifier (PGA) configured to amplify an AC voltage caused by the alternating current applied to the electrodes to measure the impedance; and a peak detector configured to detect peak-to-peak information of the amplified AC voltage.

The shared ADC uses one shared ADC to convert two types of information measured by the temperature sensor and the impedance sensor in real time.

According to another aspect of the invention, a proposed multi-electrode renal denervation method comprises the steps of: a power generator transmitting control data for adjusting temperature of a plurality of electrodes; and a catheter transmitting information measured by using an integrated circuit (IC) to the power generator, wherein the plurality of electrodes are disposed in the catheter, and the IC is incorporated in each of the plurality of electrodes and controlled by the control data received from the power generator.

In the step of the power generator transmitting the control data, frequency and phase synchronization is performed between a micro controller unit (MCU) in the power generator and the ICs incorporated in the plurality of electrodes, before the control data are transmitted; the control data are sequentially transmitted through a single wire at predetermined time intervals using a time division communication scheme; and a specific IC receiving the control data transmits the information measured by using the IC to the power generator in a next time interval, after receiving the control data.

The step of the catheter transmitting the information measured by using the IC to the power generator comprises the steps of: a regulator generating and supplying a plurality of voltages required for respective blocks in the IC, using a supply voltage supplied from the power generator through a VDD line; measuring temperature by sensing a temperature proportional current in a bandgap reference circuit of a temperature sensor; measuring impedance by an impedance sensor applying a predetermined current and sensing an absolute value of a voltage change; a shared analog-to-digital converter (ADC) digitizing information measured by the temperature sensor and the impedance sensor; digitizing the information measured by the temperature sensor and the impedance sensor and transmitting the digitized information to the power generator through the single wire; and adjusting the temperature by controlling power consumption of a heater using the control data received from the power generator according to the information measured by the temperature sensor and the impedance sensor.

In the step of measuring the temperature, temperature information is detected by sensing a temperature proportional current through a resistance.

In the step of measuring the impedance, a sine wave voltage is generated using a DDS scheme; the generated sine wave voltage is converted into a current and an alternating current is applied to the electrodes; and an AC voltage caused by the alternating current applied to the electrodes to measure the impedance is amplified to detect peak-to-peak information of the amplified AC voltage.

In the step of the shared ADC digitizing the information measured by the temperature sensor and the impedance sensor, one shared ADC is used to convert two types of information measured by the temperature sensor and the impedance sensor in real time.

In the step of adjusting the temperature, the control data received from the power generator are converted into PWM pulses through a PWM pulse generation circuit; and a plurality of MOSFET switches are controlled in parallel using the PWM pulses through a driver circuit, thereby controlling power consumption of resistance of the heater so that heat is directly transferred to a blood vessel wall through the electrodes to remove nerves.

According to embodiments of the invention, there are provided a multi-electrode renal denervation method and system using an integrated circuit, wherein a system based on a micro IC is located at the tip of a catheter and the IC is enveloped by an electrode. A temperature sensor and an impedance sensor are mounted in the IC so that information on temperature and impedance is digitally converted in the IC chip and transmitted to a display device outside a body. Thus, reliability is increased compared to a conventional method for directly transmitting an analog signal through a long wire, so that a procedure may be performed more accurately and safely, and a procedure time may be shortened by using the multiple electrodes.

DETAILED DESCRIPTION OF THE INVENTION

Figure 1:
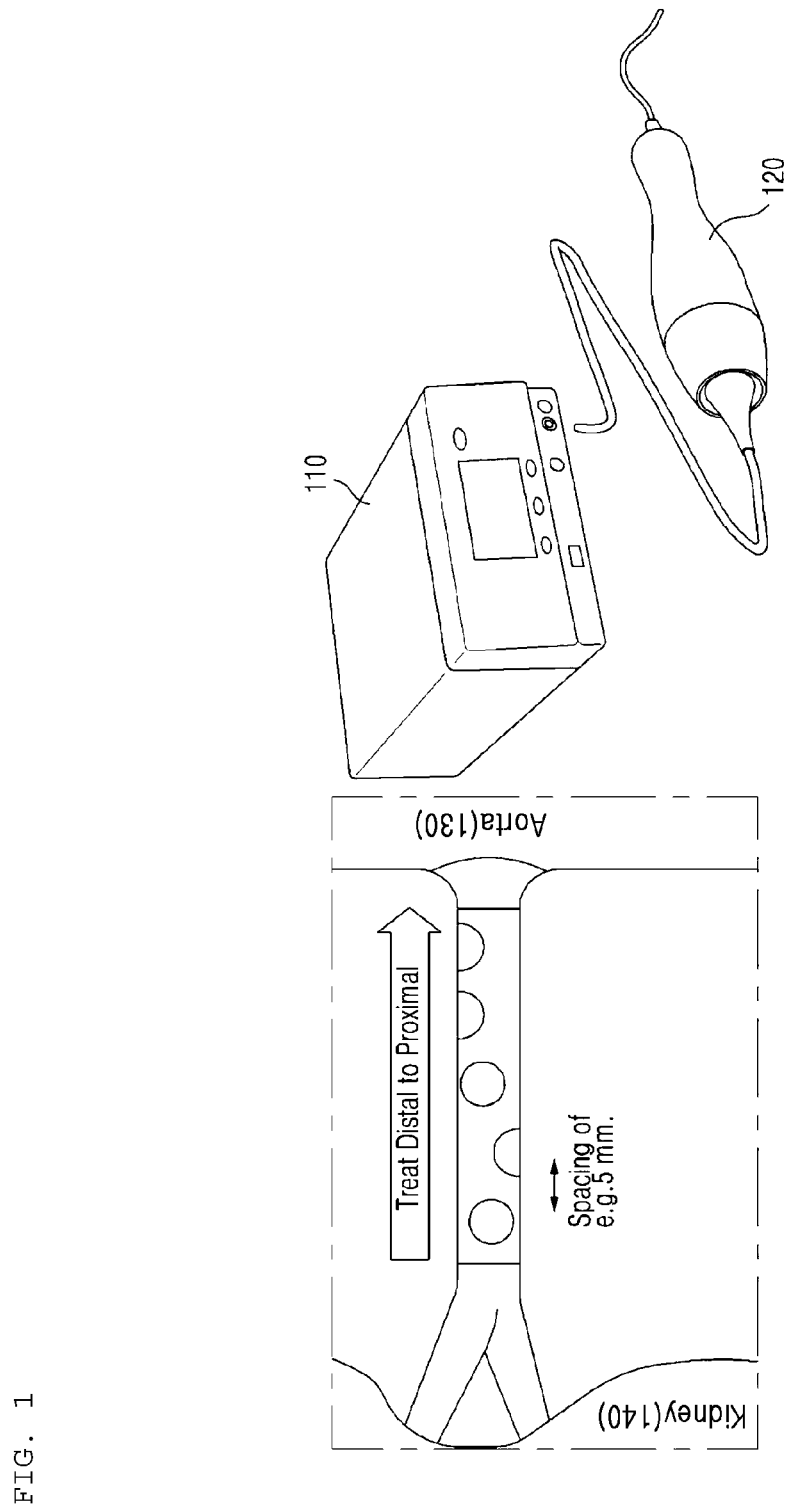
FIG. 1 illustrates an example of a conventional renal nerve block apparatus.

FIG. 1 illustrates an example of a conventional renal nerve block apparatus.

The nerve block apparatus mainly comprises a power generator 110 that generates and controls high-frequency energy outside a body, and a catheter 120 that is inserted into an artery of a kidney 140 and transfers energy to an inner wall of the artery. The catheter 120 has a long and thin structure for cutting an inguinal region and entering the artery of the kidney 140 along an aorta 130, and an electrode for transferring high-frequency energy, a temperature sensor, an impedance sensor, and the like are located at the tip of the catheter 120. High-frequency AC waves (350 to 500 kHz) generated by the power generator 110 are transmitted through the catheter 120 to transfer several watts of energy to the inside of the artery of the kidney 140, and then come out through a patch-type electrode attached outside the body. The energy is concentrated in the wall of the renal artery contacting the electrode of the catheter 120 since the wall has a high current density, while the energy is dispersed in the outer skin contacting the patch-type electrode. Because cells within the body die within 6 minutes at 50 to 60° C. and immediately destroy at 60 to 90° C., the concentrated high-frequency energy raises the temperature of the wall of the renal artery and destroys the sympathetic nerve cells. The temperature of the wall is monitored in real time and feedback information is transmitted back to the power generator 110 so that the temperature is maintained at approximately 65 to 70° C.

Hereinafter, embodiments of the present invention will be described in detail with reference to the accompanying drawings.

Figure 2:
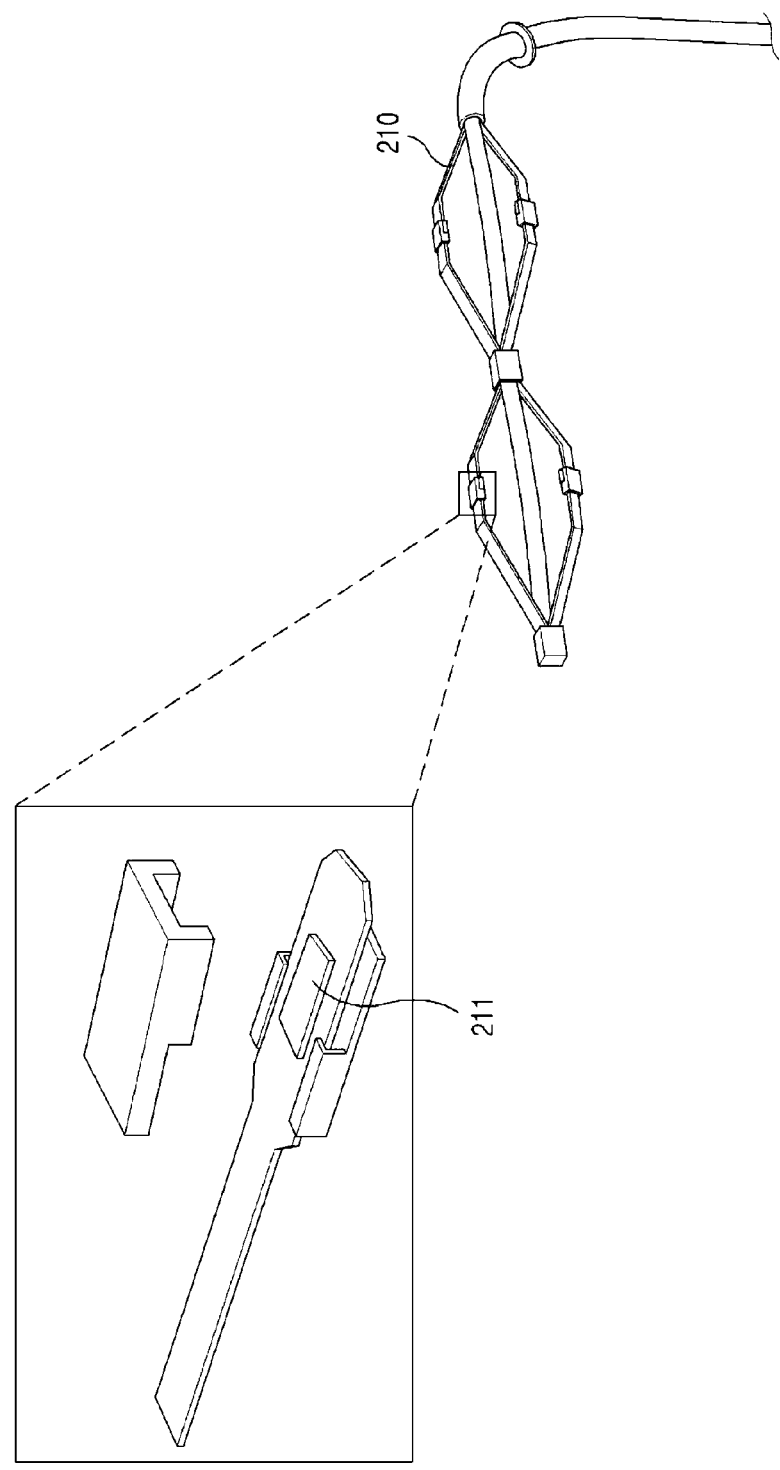
FIG. 2 illustrates a six-electrode catheter incorporating integrated circuits (ICs) according to one embodiment of the invention.

FIG. 2 illustrates a six-electrode catheter incorporating integrated circuits (ICs) according to one embodiment of the invention.

According to the invention, a system based on a micro IC 211, instead of conventional electrodes and thermocouples for temperature sensors, is located at the tip of a catheter 210. The IC 211 is mounted on a flexible PCB and enveloped by an electrode, so that it may be flexibly moved within blood vessel walls, as shown in FIG. 2. In the IC 211, a switch circuit for controlling energy from a power generator, and an on-chip temperature sensor and an impedance measurement circuit for monitoring the degree of nerve block are mounted. Information on the temperature and impedance is digitally converted in the IC chip 211 and transmitted to a display device outside the body, so that reliability is increased compared to a conventional method for directly transmitting an analog signal through a long wire. Thus, a procedure may be performed more accurately and safely.

For example, in order to shorten a procedure time, six electrodes each incorporating the IC 211 may be disposed in the catheter 210 and arranged in a circle with an interval of 60 degrees. In order to solve a problem that the number of wires is increased in proportion to the number of electrodes when multiple electrodes are used, the number of wires may be minimized by using a multiplexing technique. The multiplexing technique is a circuit technique used to maximize utility in a limited physical channel, whereby one power generator sequentially controls a plurality of electrodes with a single wire at regular time intervals. Further, a basket-type catheter is configured to stably make contact between the electrodes and blood vessel walls within blood vessels, and may be easily controlled during a procedure.

Like the example of the conventional renal nerve block apparatus shown in FIG. 1, the multi-electrode renal denervation system using the proposed IC may comprise a power generator 110 and a catheter 120.

However, unlike the prior art, the power generator of the multi-electrode renal denervation system using the proposed IC is configured to sequentially transmit control data for controlling temperature of a plurality of electrodes through a single wire at predetermined time intervals, and the catheter is configured to digitize information measured by using the IC and transmit the digitized information to the power generator through the single wire, wherein the plurality of electrodes are disposed in the catheter, and the IC is incorporated in each of the plurality of electrodes and controlled by the control data received from the power generator.

The IC is connected to the power generator using a VDD line for supplying a supply voltage, a GND line, and a data line for data communication. A plurality of voltages required for the respective blocks in the IC are generated from the supply voltage supplied through the VDD line using a regulator in the IC, and supplied to the respective blocks.

Here, the data line for data communication is a single wire that enables bidirectional communication between the power generator and the plurality of ICs using a time division communication scheme.

The control data are in the form of packets transmitted from a micro controller unit (MCU) in the power generator. The packets have predetermined ID data, and the ID data indicate that the control data are transmitted to a specific IC corresponding to a predetermined ID, among the ICs incorporated in the plurality of electrodes.

Before the control data are transmitted, frequency and phase synchronization is performed between the MCU in the power generator and the ICs incorporated in the plurality of electrodes. Further, the specific IC receiving the control data may transmit the information measured by using the IC to the power generator in a next time interval, after receiving the control data.

Figure 3:
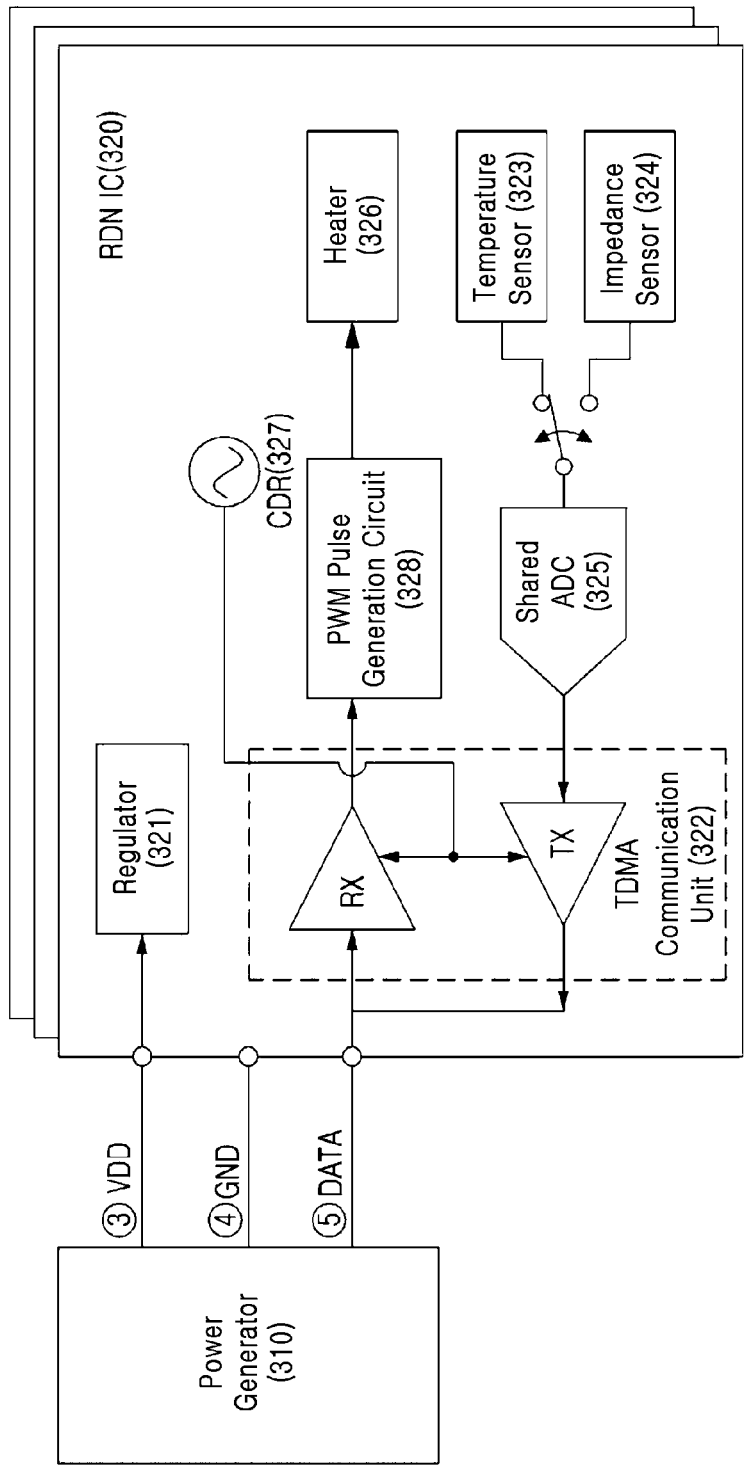
FIG. 3 illustrates a system block diagram of a renal denervation (RDN) IC according to one embodiment of the invention.

FIG. 3 illustrates a system block diagram of a renal denervation (RDN) IC according to one embodiment of the invention.

A proposed IC 320 comprises a regulator 321, a communication unit 322, a temperature sensor 323, an impedance sensor 324, a shared analog-to-digital converter (ADC) 325, a heater 326, a clock and data recovery (CDR) circuit 327, and a PWM pulse generation circuit 328.

The regulator 321 is configured to generate and supply a plurality of voltages required for the respective blocks in the IC 320 using a supply voltage supplied from the power generator 310 through a VDD line.

The communication unit 322, which includes a receiver RX and a transmitter TX, is configured to receive control data from the power generator 310 and to transmit information measured by using the temperature sensor 323 and the impedance sensor 324 to the power generator through a single wire.

The temperature sensor 323 is configured to measure temperature using a temperature proportional current in a bandgap reference circuit. The temperature sensor 323 is utilized to increase an amount of a supply current of the heater when the measured temperature is lower than a target temperature, and to decrease the amount of the supply current of the heater when the measured temperature is higher than the target temperature.

The impedance sensor 324 is configured to measure impedance by applying a predetermined current and sensing an absolute value of a voltage change. The impedance sensor 324 comprises a digital sine wave generator configured to generate a sine wave voltage using a DDS scheme; an alternating current application circuit configured to convert the generated sine wave voltage into a current and apply an alternating current to the electrodes; a programmable gain amplifier (PGA) configured to amplify an AC voltage caused by the alternating current applied to the electrodes to measure the impedance; and a peak detector configured to detect peak-to-peak information of the amplified AC voltage.

The shared ADC 325 is configured to digitize the information measured by the temperature sensor 323 and the impedance sensor 324. One shared ADC 325 is used to convert two types of information specified by the temperature sensor 323 and the impedance sensor 324 in real time.

The heater 326 is configured to adjust the temperature by controlling power consumption using the control data received from the power generator 310. The heater 326 converts the control data received from the power generator 310 into PWM pulses through the PWM pulse generation circuit, and controls a plurality of MOSFET switches in parallel using the PWM pulses through a driver circuit, thereby controlling power consumption of resistance of the heater 326. By controlling the power consumption of the resistance of the heater 326, heat is directly transferred to a blood vessel wall through the electrodes to remove nerves.

In other words, the external power generator 310 and the ICs 320 incorporated in the electrodes are connected by three wires, i.e., a VDD line for supplying power, a GND line, and a DATA line for data communication. Although a plurality of power domains are needed to drive the ICs 320, an internal regulator is used to generate a necessary supply voltage and supply it to each block, in order to minimize the number of wires. Data communication may be implemented with a TDMA scheme using a single wire, which enables one-to-many bidirectional communication.

The power generator 310 sends the control data to adjust the temperature of the electrodes, and the control data are recovered using a clock and data recovery (CDR) circuit that operates without an external reference clock. The interpreted data are converted into PWM pulses to control the heater 326. The temperature of the electrodes is always monitored by the temperature sensor 323 in the IC 320, and digitized together with the impedance information by the one shared ADC 325 to be outwardly transmitted. Since the temperature information and impedance information sensed by each of the ICs 320 are sequentially transmitted over time using the TDMA scheme, they may be transmitted to the power generator 310 without interference or conflict with each other.

Figure 4:
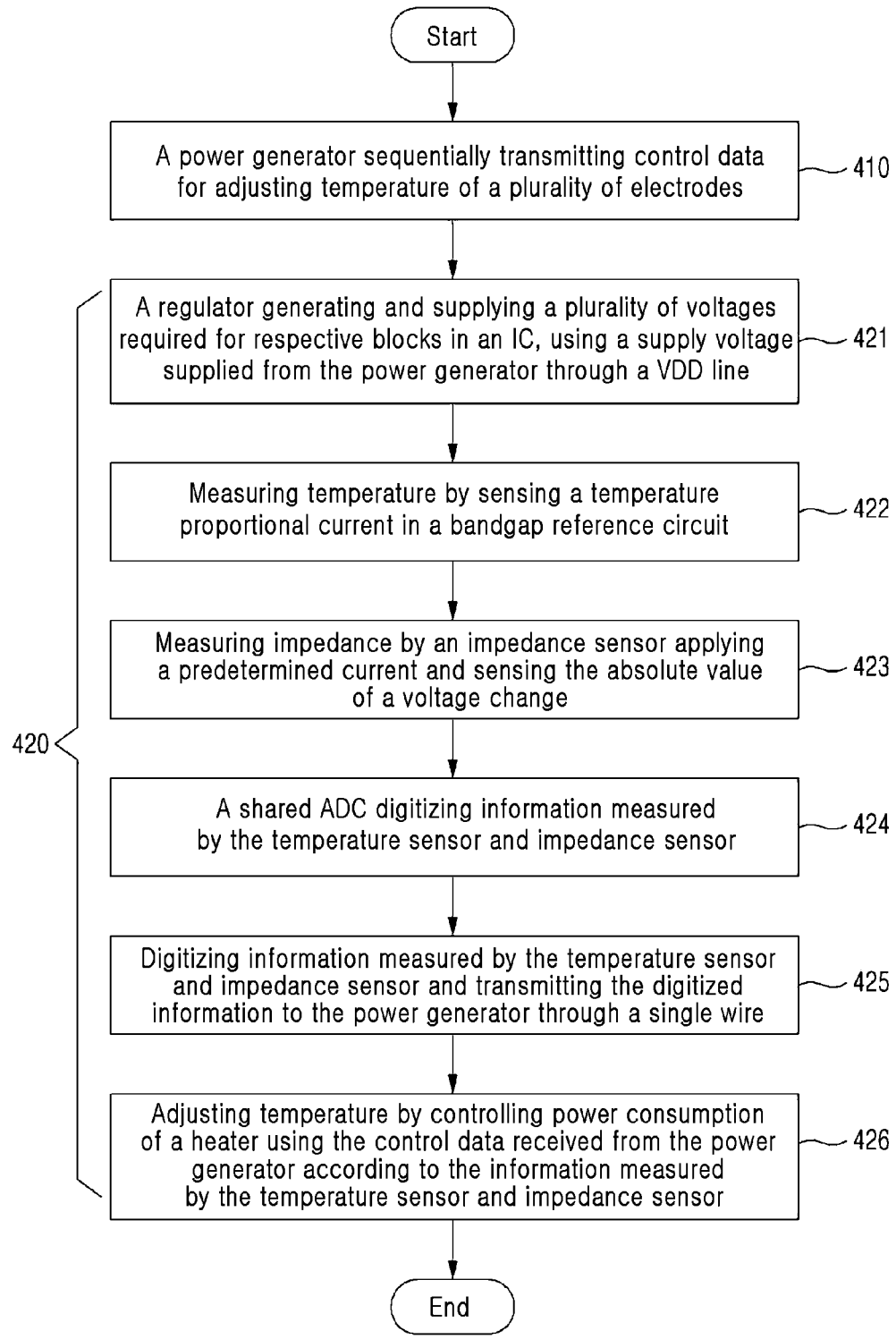
FIG. 4 is a flowchart for illustrating a multi-electrode renal denervation method using an IC according to one embodiment of the invention.

FIG. 4 is a flowchart for illustrating a multi-electrode renal denervation method using an IC according to one embodiment of the invention.

A multi-electrode renal denervation method using a proposed IC may comprise a step 410 of a power generator sequentially transmitting control data for adjusting temperature of a plurality of electrodes through a single wire at predetermined time intervals, and a step 420 of a catheter digitizing information measured by using an IC and transmitting the digitized information to the power generator through the single wire, wherein the plurality of electrodes are disposed in the catheter, and the IC is incorporated in each of the plurality of electrodes and controlled by the control data received from the power generator.

In the step 410, before the control data are transmitted, frequency and phase synchronization is performed between a micro controller unit (MCU) in the power generator and the ICs incorporated in the plurality of electrodes. Further, a specific IC receiving the control data transmits the information measured by using the IC to the power generator in a next time interval, after receiving the control data.

The step 420 comprises a step 421 of a regulator generating and supplying a plurality of voltages required for the respective blocks in the IC using a supply voltage supplied from the power generator through a VDD line; a step 422 of measuring temperature by sensing a temperature proportional current in a bandgap reference circuit of a temperature sensor; a step 423 of measuring impedance by an impedance sensor applying a predetermined current and sensing an absolute value of a voltage change; a step 424 of a shared analog-to-digital converter (ADC) digitizing the information measured by the temperature sensor and the impedance sensor; and a step 425 of digitizing the information measured by the temperature sensor and the impedance sensor and transmitting the digitized information to the power generator through the single wire; and a step 426 of adjusting the temperature by controlling power consumption of a heater using the control data received from the power generator according to the information measured by the temperature sensor and the impedance sensor.

In the step 422, in addition to measuring the temperature, an amount of a supply current of the heater may be increased when the measured temperature is lower than a target temperature, and decreased when the measured temperature is higher than the target temperature.

In the step 423, a sine wave voltage is generated using a DDS scheme; the generated sine wave voltage is converted into a current and an alternating current is applied to the electrodes; and an AC voltage caused by the alternating current applied to the electrodes to measure the impedance is amplified to detect peak-to-peak information of the amplified AC voltage.

In the step 424, one shared ADC is used to convert two types of information measured by the temperature sensor and the impedance sensor in real time.

In the step 426, the control data received from the power generator are converted into PWM pulses through a PWM pulse generation circuit, and a plurality of MOSFET switches are controlled in parallel using the PWM pulses through a driver circuit, thereby controlling power consumption of resistance of the heater. By controlling the power consumption of the resistance, heat is directly transferred to a blood vessel wall through the electrodes to remove nerves. Hereinafter, a multi-electrode renal denervation method and system using a proposed IC will be discussed in more detail, with reference to FIGS. 5A to 22.

Figure 5A:
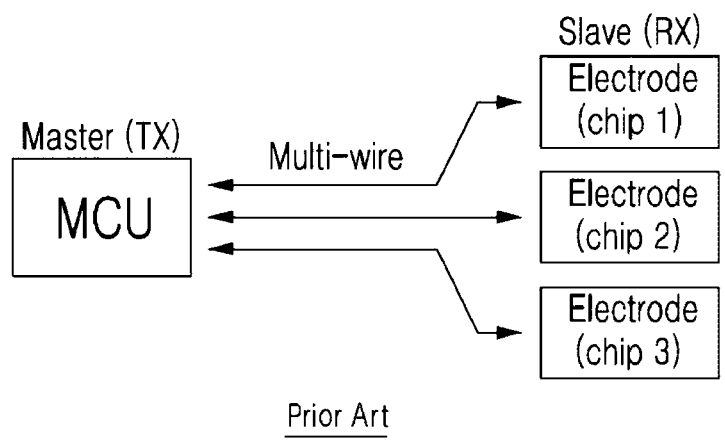
FIG. 5A illustrates a conventional multi-electrode system using multiple electrodes and sensors.

FIG. 5A shows an example of a conventional multi-electrode system using multiple electrodes and sensors. Although the conventional multi-electrode system using multiple electrodes and sensors may shorten a procedure time, the number of wires connected to an external control device, i.e., a MCU (Master (TX)) of a power generator, is increased in proportion to the number of electrodes. The multiple wires increase the diameter of a catheter that should pass through blood vessels, so that a procedure cannot be efficiently performed and the yield of a process for manufacturing an apparatus is reduced to increase the cost of the apparatus.

Figure 5B:
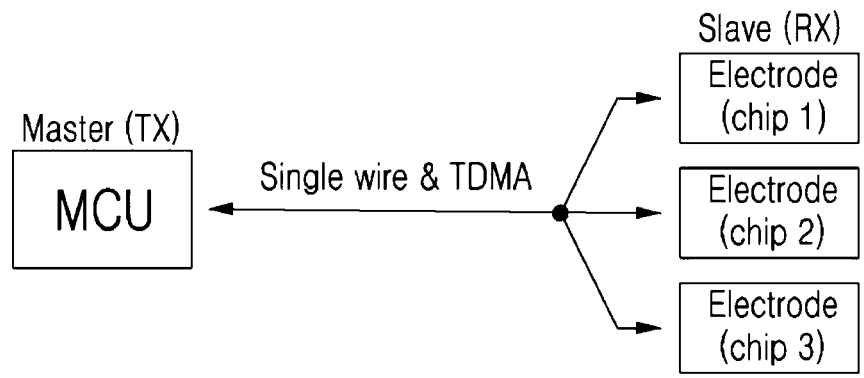
FIG. 5B illustrates a time division communication scheme according to one embodiment of the invention.

FIG. 5B shows a time division communication scheme of a multi-electrode renal denervation system using a proposed IC. Data communication is required in order for an external control device, i.e., the MCU (Master (TX)) of the power generator, to control heaters of multiple ICs (chip 1, chip 2, chip 3) incorporated in electrodes (Slave (RX)) and to outwardly transmit information on temperature and impedance measured within a body. When multiple electrodes are used, the number of wires for the communication is also increased in proportion to the number of electrodes. However, in the proposed invention, bidirectional communication may be implemented with a single wire using a time division communication scheme.

Figure 6A:
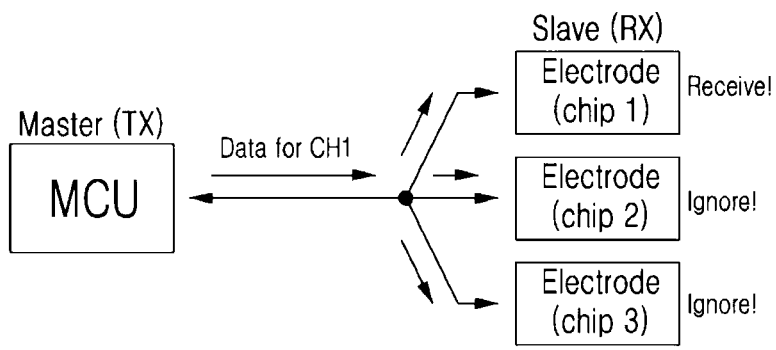
FIG. 6A illustrates processes of data transmission and reception according to one embodiment of the invention.
Figure 6B:
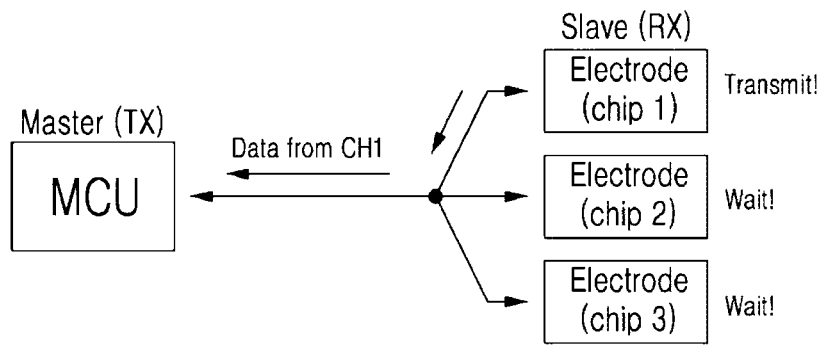
FIG. 6B illustrates processes of data transmission and reception according to one embodiment of the invention.
Figure 6C:
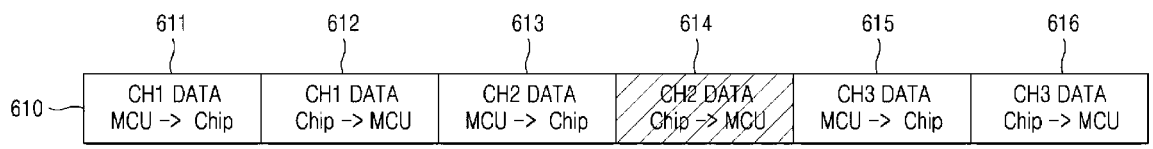
FIG. 6C illustrates processes of data transmission and reception according to one embodiment of the invention.

FIGS. 6A to 6C illustrate processes of data transmission and reception according to one embodiment of the invention.

FIG. 6A shows that control data are transmitted from a MCU (Master (TX)) of a power generator to heaters of multiple ICs (chip 1, chip 2, chip 3) incorporated in electrodes (Slave (RX)).

FIG. 6B shows that information on measured temperature and impedance is transmitted from the multiple ICs (chip 1, chip 2, chip 3) incorporated in the electrodes (Slave (RX)) to the MCU (Master (TX)) of the power generator.

The control data sent from the MCU (Master (TX)) of the power generator to the multiple ICs (chip 1, chip 2, chip 3) of the respective electrodes are in the form of packets 610, and each packet 611, 612, 613, 614, 615, 616 has ID data for a specific IC, which specify that the control data are sent to the specific IC among the multiple ICs. As shown in FIGS. 6A to 6C, all the ICs receive the same data through a single wire, but only one IC having a matched ID processes the data. The IC having received the data outwardly transmits information on the measured temperature and impedance through the packet 614 in a next time interval. Thus, data sent from the MCU to each IC and data sent from each IC to the MCU are sequentially transmitted through the single wire, without overlaps or blanks.

Figure 7:
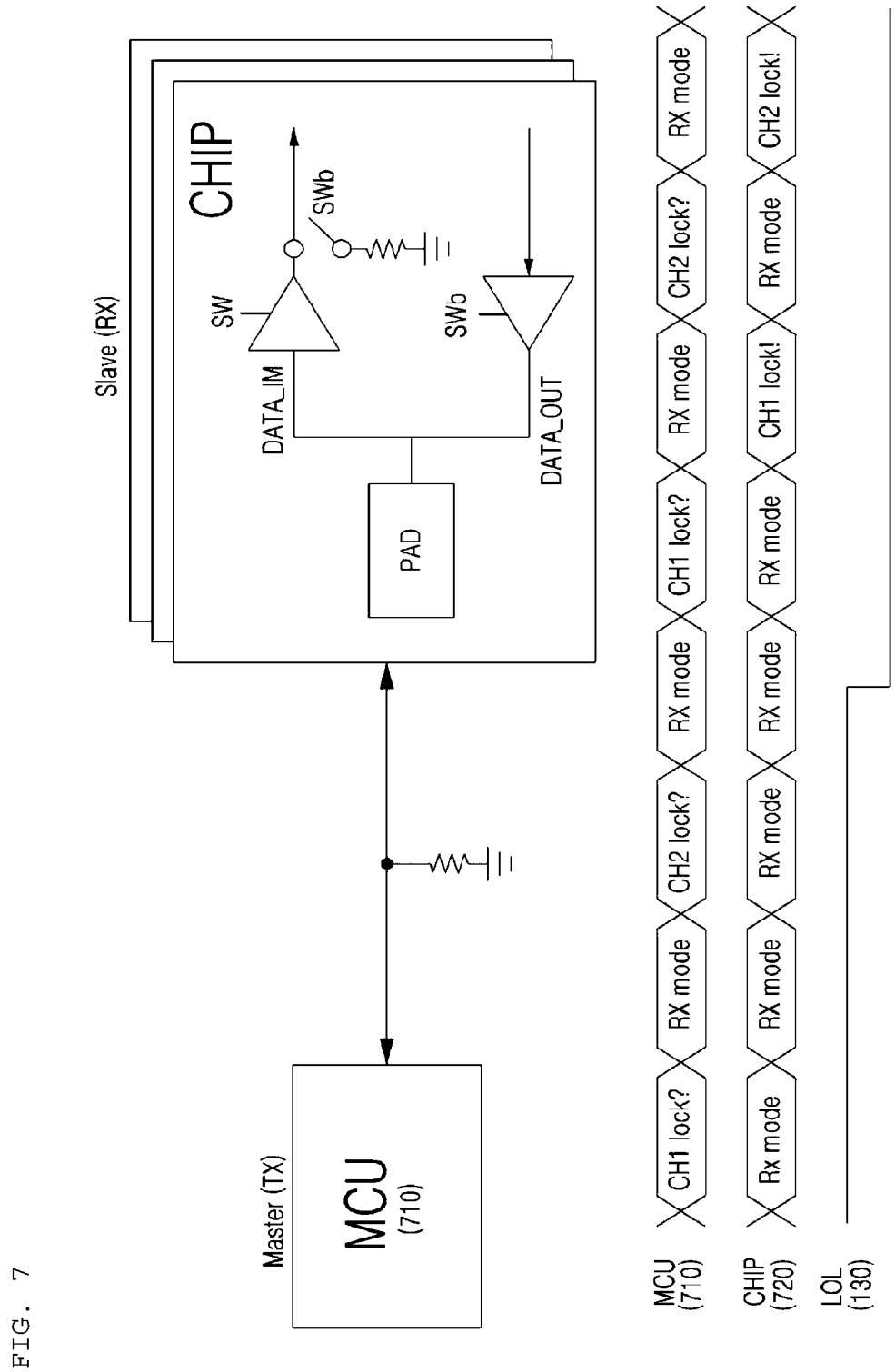
FIG. 7 illustrates a frequency and phase synchronization check process according to one embodiment of the invention.

FIG. 7 illustrates a frequency and phase synchronization check process according to one embodiment of the invention.

In order to perform data communication, a clock and data recovery (CDR) circuit is required because frequency and phase information of data to be transmitted and received should match. The CDR circuit requires a certain amount of time for frequency and phase synchronization, and a loss of lock (LOL) detector block included therein monitors in real time whether the synchronization is made. Thus, a process of checking synchronization information from the LOL before starting data communication is required. The MCU sequentially sends each IC data for checking whether the synchronization is made, and the IC extracts the frequency and phase information from the data. When the synchronization is complete, each IC informs the MCU that the synchronization is complete. The synchronization completion timing may be different for each IC, and the MCU starts data communication for a procedure after confirming that all the ICs are synchronized.

Figure 8:
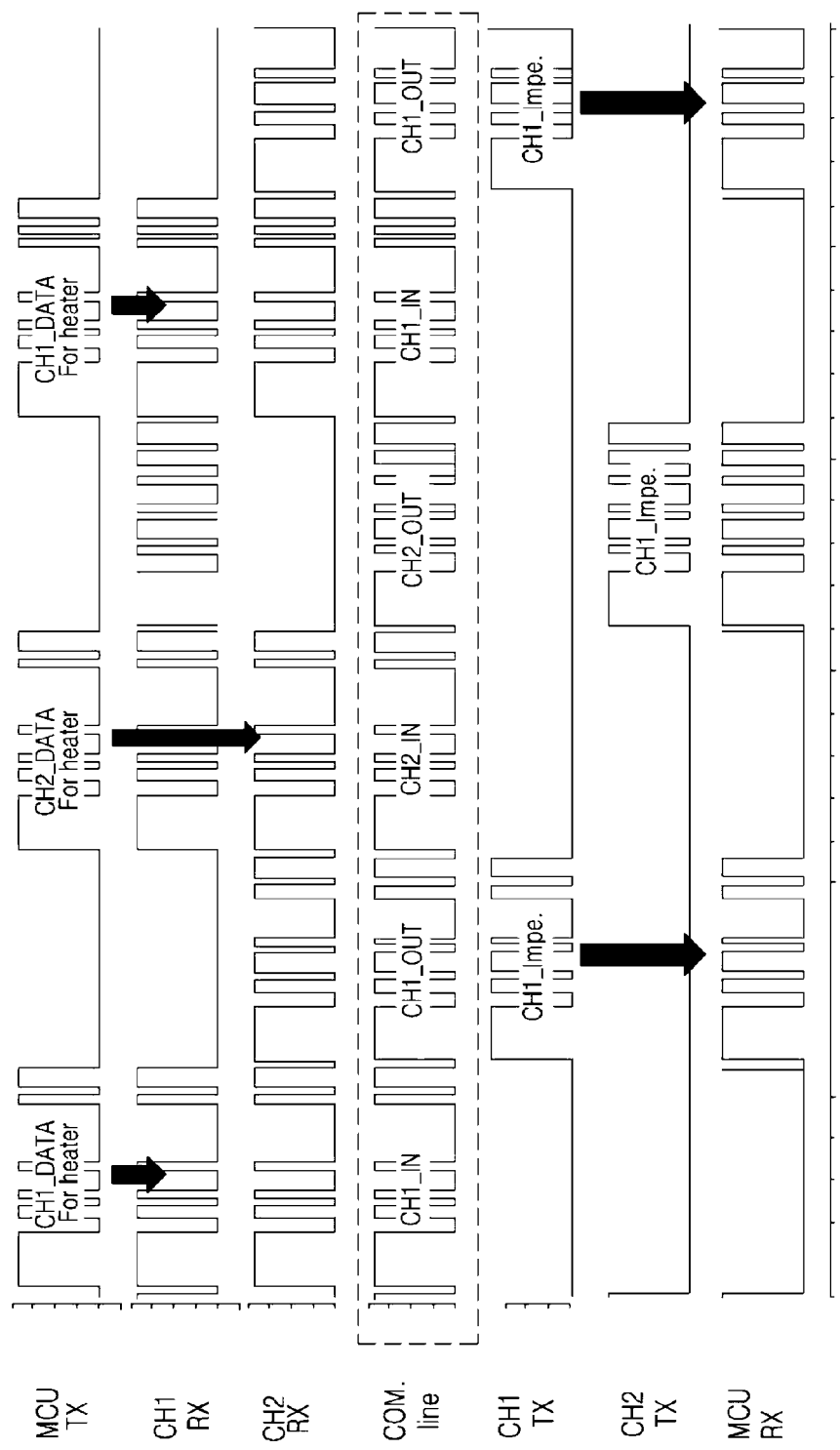
FIG. 8 illustrates a result of a data communication simulation according to one embodiment of the invention.

FIG. 8 illustrates a result of a data communication simulation according to one embodiment of the invention.

Data sent from a transmitter (TX) of the MCU are transmitted to receivers (RX) of both IC1 and IC2. However, each IC first analyzes the ID data and processes only the data sent to the corresponding IC. The data sent from a TX of each IC are sequentially transmitted to a RX of the MCU, and it can be seen that one-to-many bidirectional communication may be implemented through a single data line.

Figure 9:
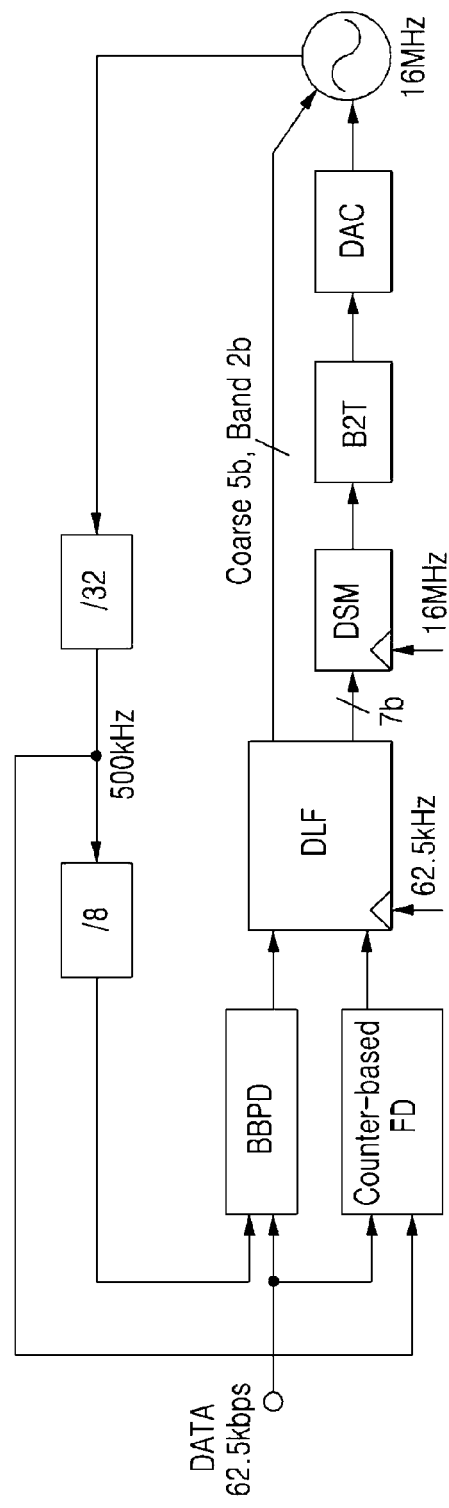
FIG. 9 illustrates the structure of a clock and data recovery (CDR) circuit according to one embodiment of the invention.

FIG. 9 illustrates the structure of a clock and data recovery (CDR) circuit according to one embodiment of the invention.

Generally, a CDR circuit requires an external reference clock. However, the present invention employs a structure for synchronizing frequencies and phases without using any reference clock, in order to minimize the number of externally connected wires. Update information of a bang-bang type phase detector (BBPD) and a frequency detector (FD) controls a voltage controlled oscillator (VCO) through a digital loop filter (DLF). For example, the VCO may have three control paths. Among the control paths, the path for the finest control performs delta-sigma modulation (DSM) in order to overcome resolution limits, and the result is converted into a thermometer code and then changed to an analog voltage in order to minimize glitches.

Figure 10:
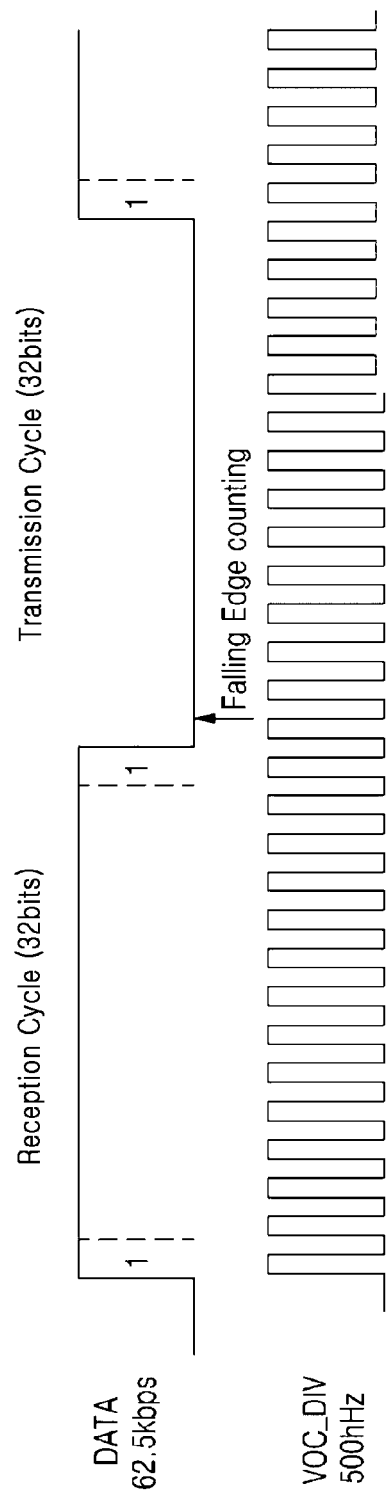
FIG. 10 illustrates the principle of a counter-based frequency detector according to one embodiment of the invention.

FIG. 10 illustrates the principle of a counter-based frequency detector according to one embodiment of the invention.

Generally, in order to extract frequency information from data without a reference clock, it is necessary to continuously receive the data. Thus, it is difficult to use a conventional scheme in the present invention, because the invention performs bidirectional communication using a single wire. Since the present invention performs data communication using a time division scheme, a cycle for receiving input data and a cycle for outputting output data are always constant. Accordingly, when a start bit and an end bit of the input data are set to 1, and an output interval is set to 0 by using a pull down resistor, a continuous interval that is constantly 0 may be formed as shown in FIG. 10. The continuous interval may be counted using a frequency-divided VCO clock and compared with an ideal value to determine whether the current VCO frequency is higher or lower than the frequency of the input data.

Figure 11:
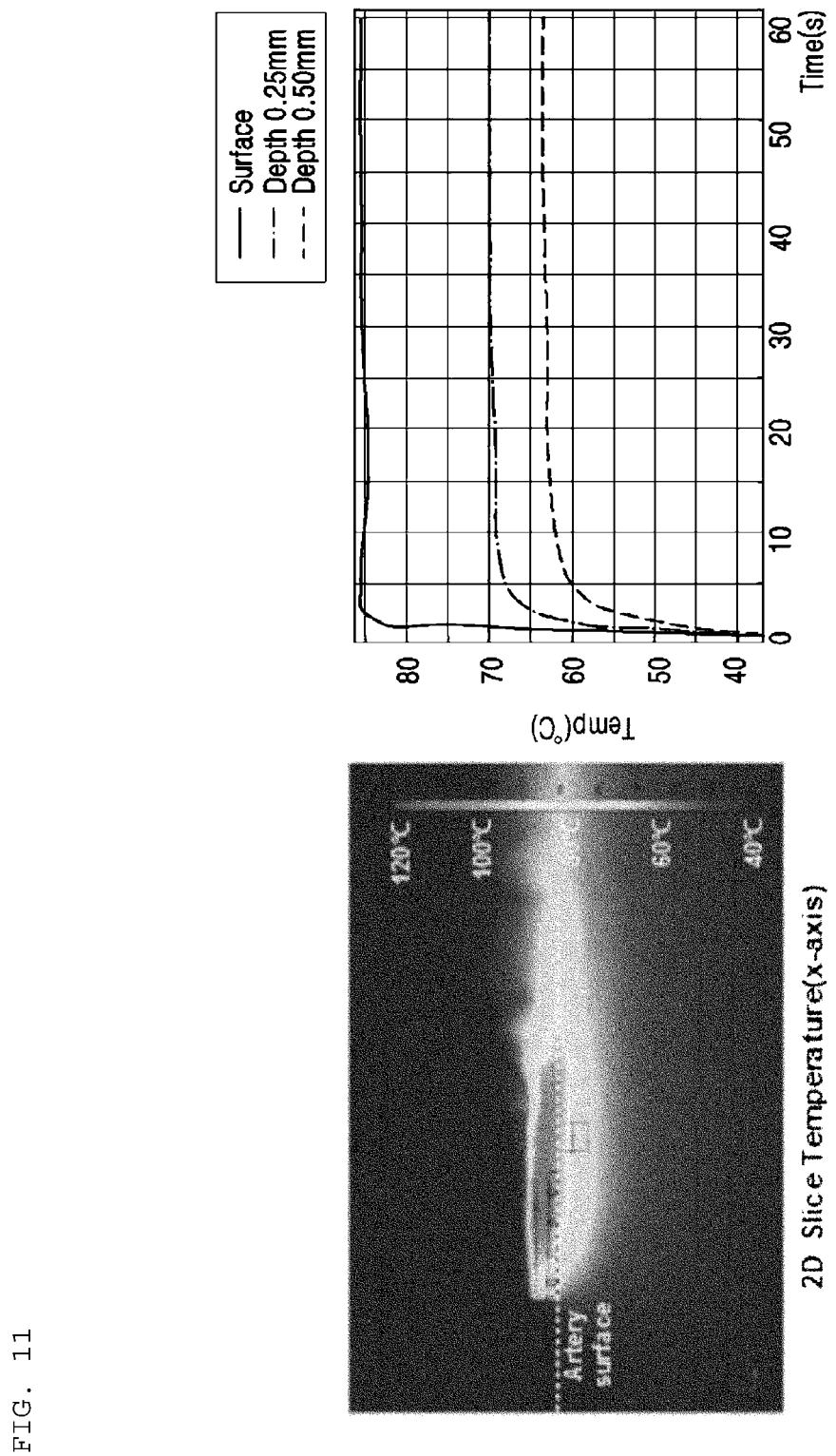
FIG. 11 illustrates a simulation result of a 3D finite element solver according to one embodiment of the invention.

FIG. 11 illustrates a simulation result of a 3D finite element solver according to one embodiment of the invention.

In a RF (Radio Frequency) ablation technique for transferring high-frequency AC energy into a body to remove nerves, a current density and an energy concentration are determined according to an area of an electrode. Thus, a skin burn may occur depending on a contact state of a patch-type electrode attached outside the body, and an AC signal flowing into the body may interfere with another monitoring apparatus. Further, in order to use a multiplexing technique for controlling multiple electrodes with a single wire, an AC control switch should be implemented within an IC. However, since a high-voltage AC switch occupies a large area, it is inefficient to implement the switch with an IC. Thus, the present invention employs a direct heating technique in which heat is directly generated and transferred by an IC. The temperature of the IC is increased in proportion to power consumption. Therefore, the power consumption of a heater circuit implemented within the IC is adjusted according to the input.

FIG. 11 shows a result of a simulation of a temperature change according to the IC power consumption using a 3D finite element solver. When the heater circuit within the IC consumes a certain amount of power, the temperature of the electrode gradually increases from a body temperature of 36.5° C., and then stops increasing and converges due to the cooling action of flowing blood. Through the simulation, the amount of power to be consumed to heat a blood vessel wall to a desired temperature may be predicted.

Figure 12:
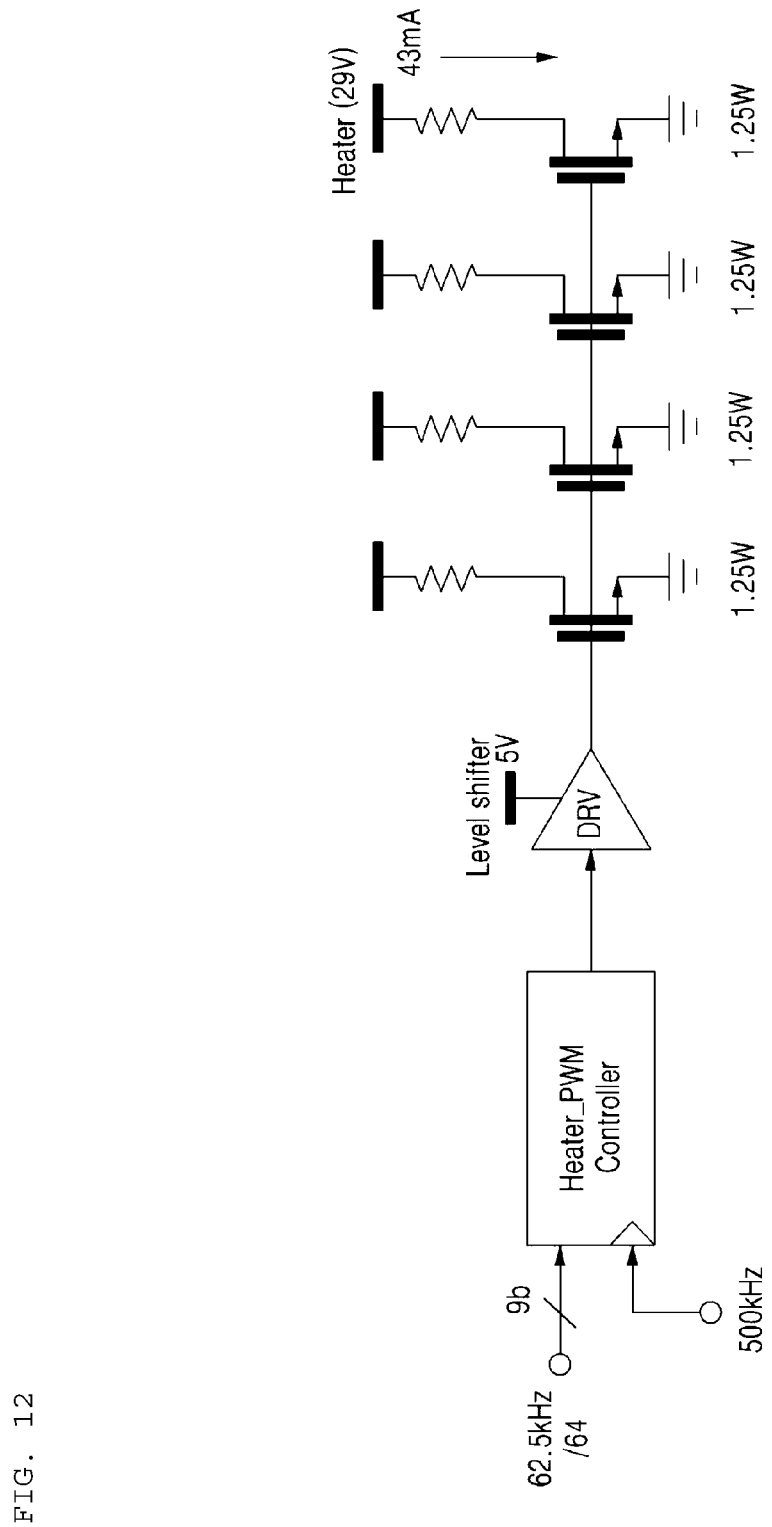
FIG. 12 illustrates the structure of a heater circuit according to one embodiment of the invention.

FIG. 12 illustrates the structure of a heater circuit according to one embodiment of the invention.

A proposed heater circuit includes a plurality of resistors capable of generating heat, MOSFET switches for controlling the plurality of resistors, and a PWM pulse generation circuit (Heater_PWM Controller). For example, four heater circuits consuming up to 1.25 W of power may be evenly distributed within the IC to consume up to 5 W of power. 9-bit data transmitted from the MCU are converted into PWM pulses to control the MOSFET switches in parallel through a driver circuit (DRV). The relationship between the power consumption and the duty cycle of the PWM pulses is as below.

Power consumption $(W)=5W\times$duty cycle

Figure 13:
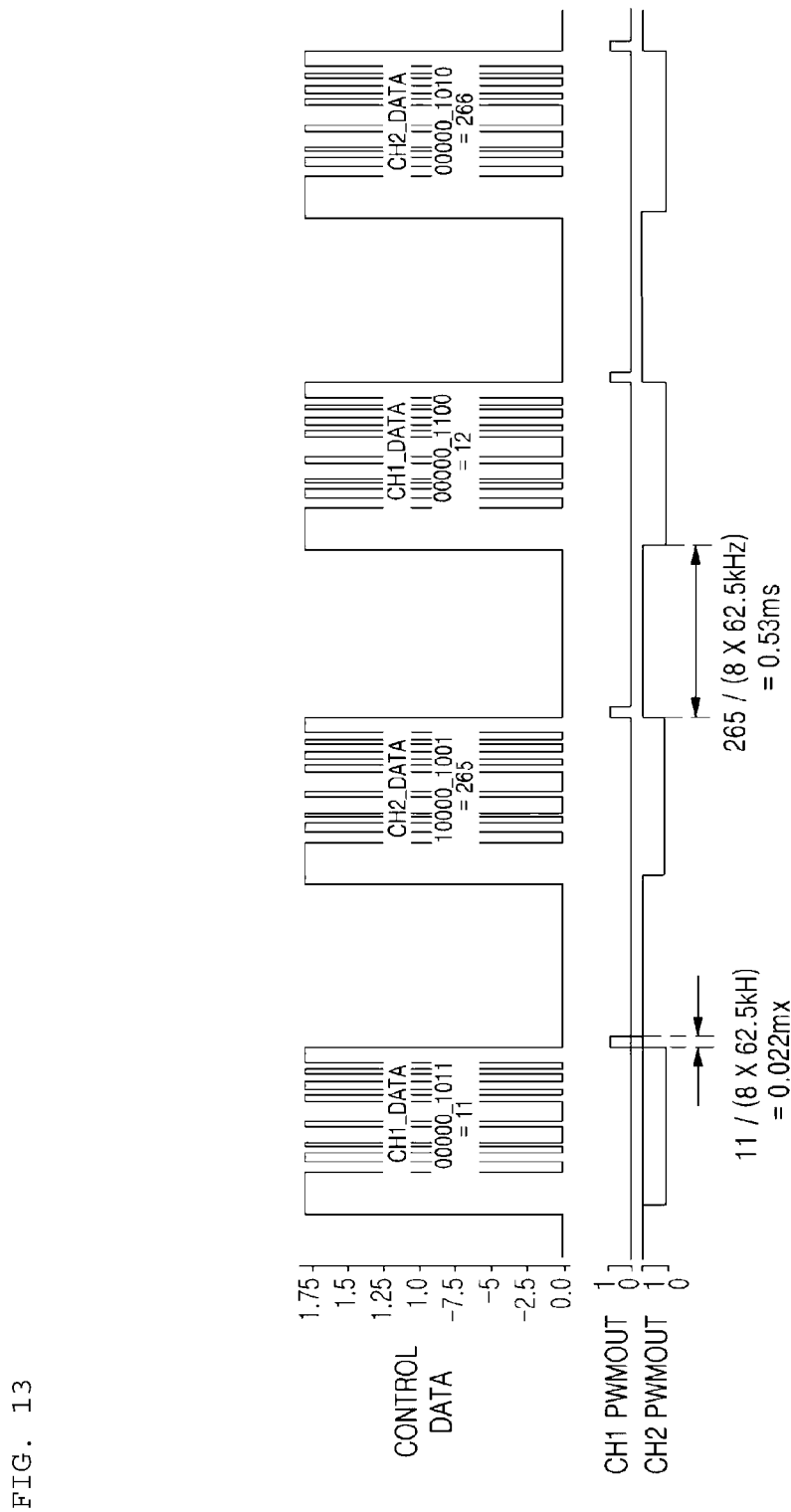
FIG. 13 illustrates a simulation result of a PWM control circuit according to one embodiment of the invention.

FIG. 13 illustrates a simulation result of a PWM control circuit according to one embodiment of the invention.

According to one embodiment of the invention, it can be seen that a PWM pulse is formed with respect to a falling edge of the last bit of the transmitted data, and the cycle of the pulse is data/(8×62.5 kHz).

Figure 14:
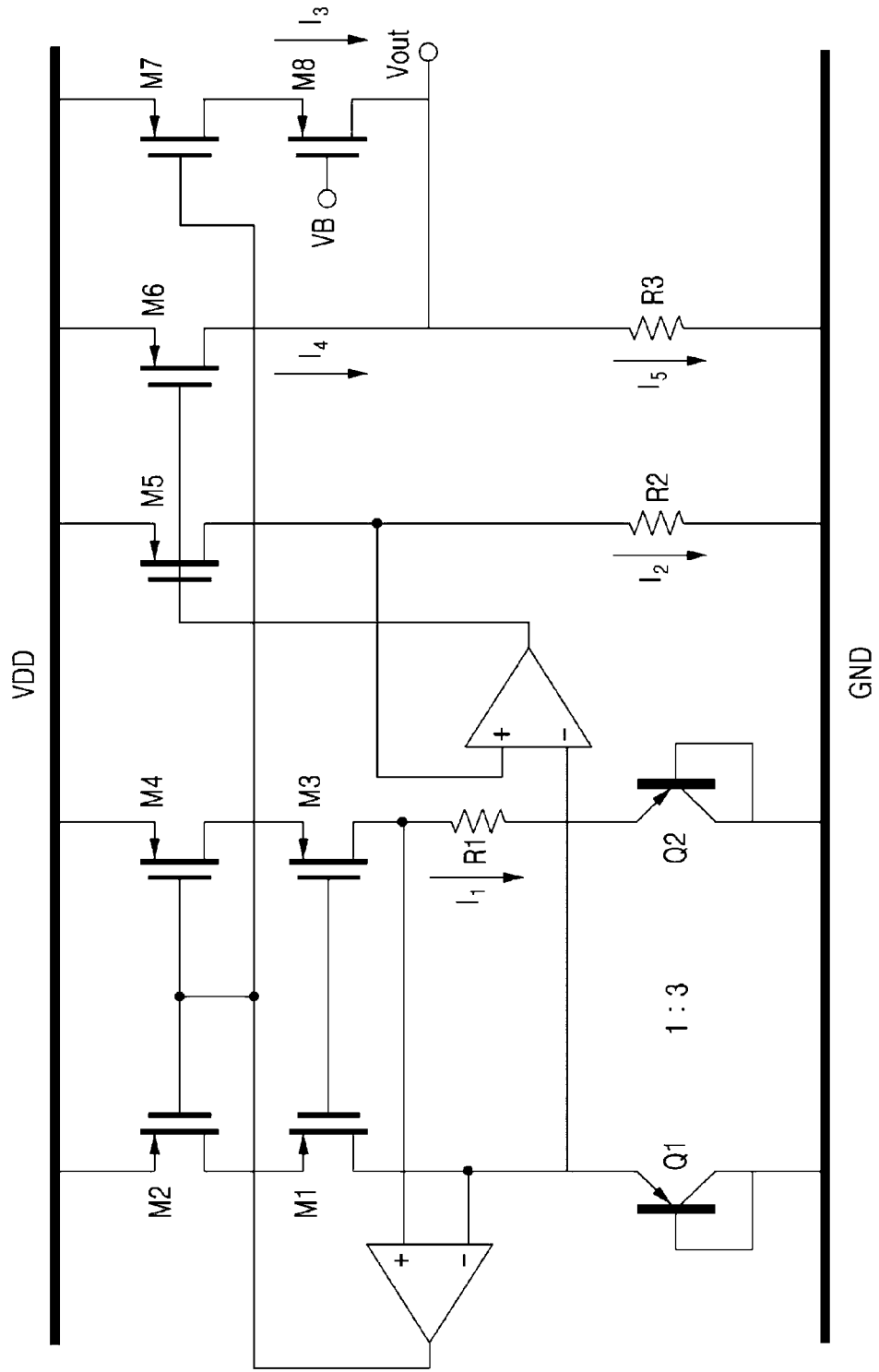
FIG. 14 illustrates a bandgap reference circuit according to one embodiment of the invention.

FIG. 14 illustrates a bandgap reference circuit according to one embodiment of the invention.

The entire heating mechanism consists of a feedback system using temperature information. In order to block nerves of a renal artery wall, an appropriate temperature should be maintained for a certain period of time. Generally, heating at about 60 to 70° C. for about 1 minute may produce a desired degree of lesion. An excessively high temperature causes carbonization of endarterial layers, and an excessively low temperature may not achieve removal of the nerves. In order to maintain a constant temperature, the feedback system compares a constant reference temperature with temperature information obtained through a temperature sensor to increase the power when the temperature of the vessel wall is lower, and to reduce the power when the temperature of the vessel wall is higher, so that the temperature converges to the desired reference temperature. For such a negative feedback system, a temperature sensor for sensing temperature information is required.

An on-chip temperature sensor of the invention mainly uses characteristics of how various parameters of MOSFETs or BJTs are changed depending on the temperature. Among various techniques for sensing temperature information, there is a technique in which a voltage generated in a bandgap is used so that an absolute value thereof may be predicted in advance. FIG. 14 shows a circuit for generating a bandgap reference voltage. For example, the slopes of a PTAT (Proportional To Absolute Temperature) current (I3) uniformly increasing with the temperature and a CTAT (Complementary To Absolute Temperature) current (I4) uniformly decreasing with the temperature are made equal, and then the two currents are flowed into resistors to produce a voltage (I5) not varying with the temperature. A temperature sensor based on such a bandgap circuit usually senses the temperature by using the characteristics of the PTAT or CTAT current varying with the temperature at a constant slope.

Figure 15:
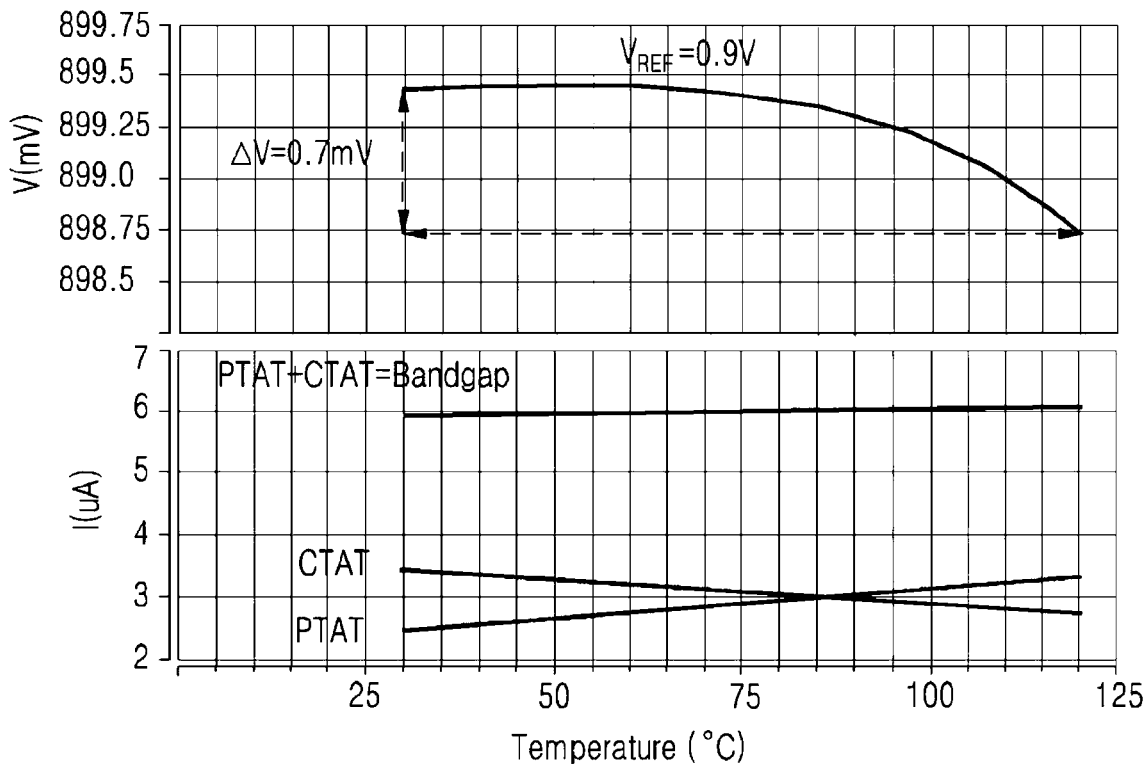
FIG. 15 illustrates a simulation result of a temperature sensor according to one embodiment of the invention.
Figure 15:
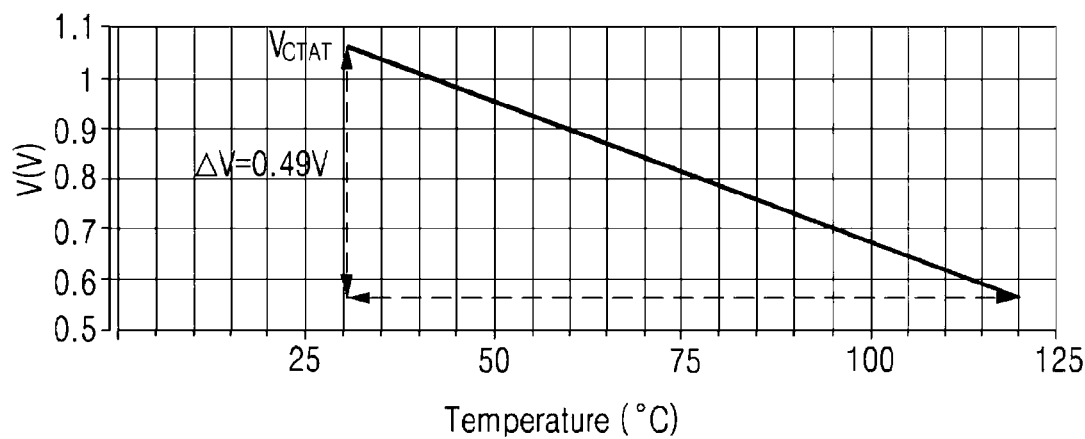

FIG. 15 illustrates a simulation result of a temperature sensor according to one embodiment of the invention.

It can be seen that a bandgap voltage according to one embodiment of the invention exhibits a minute voltage change of about 0.7 mV as the temperature is changed, and the output voltage of the temperature sensor uniformly decreases between 30 and 120° C.

Figure 16:
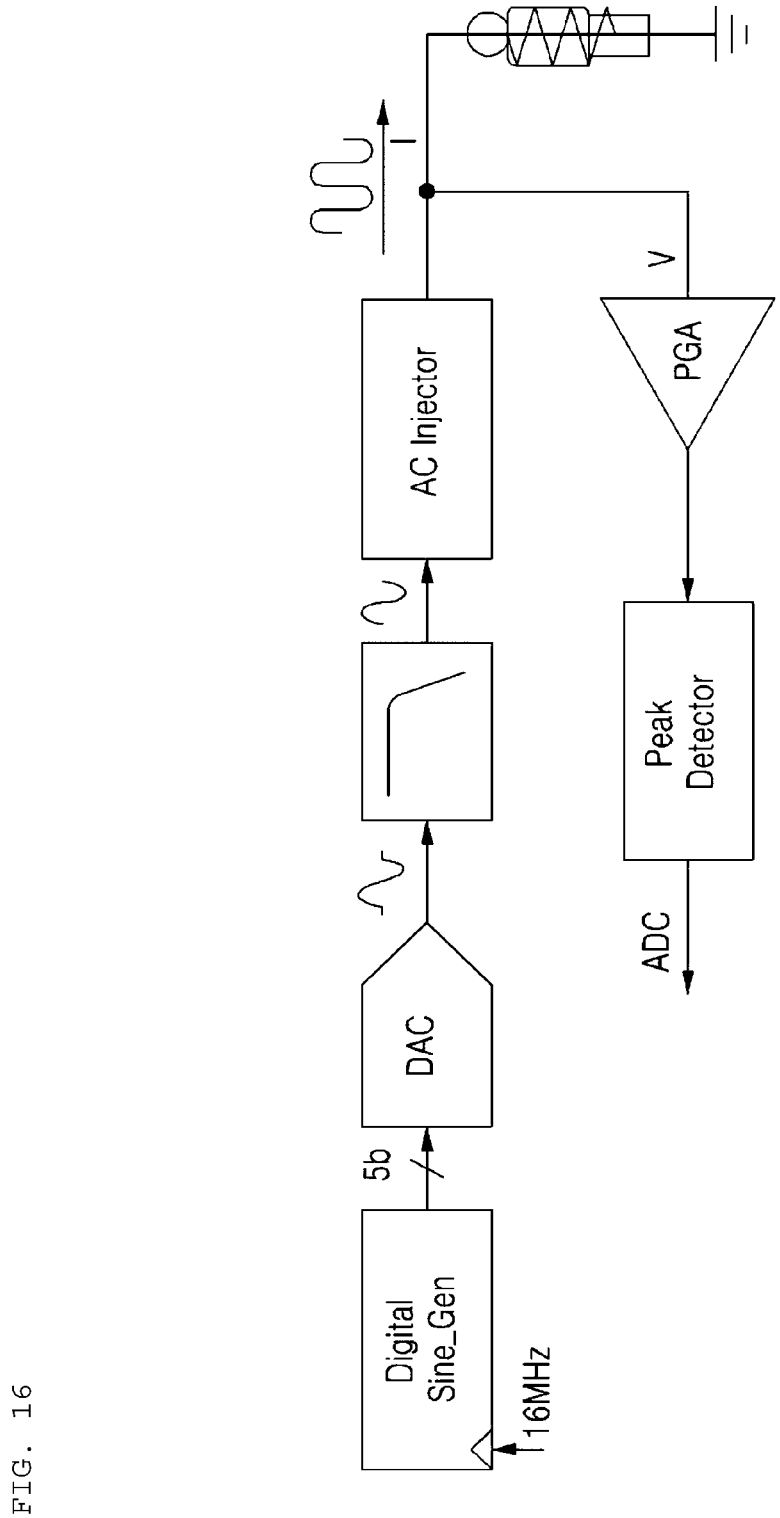
FIG. 16 illustrates an impedance sensing process according to one embodiment of the invention.

FIG. 16 illustrates an impedance sensing process according to one embodiment of the invention.

In a nerve block procedure, impedance information is used as a criterion for determining whether contact between an electrode and a blood vessel wall tissue has been effectively made. As the vessel wall tissue is normally heated, a temperature-dependent decrease in electrical impedance occurs. An abrupt increase in the impedance is indicative of tissue carbonation or clot formation. Thus, observing the impedance of the surface of the tissue is essential as it is a process of obtaining information on a procedure state between the electrode and the surface. The impedance may be measured by applying a voltage to a current loop, which consists of a patch attached to a thigh, an electrode in contact with a blood vessel wall, and a human body, and then reading a current, or by applying a current and then reading a voltage change. In the embodiment of the invention, an arbitrary known current is applied and the absolute value of a voltage change is sensed to measure the impedance.

According to medical regulations (IEC 60601-1), the maximum allowable current that may be applied to a human body for a measurement purpose is limited to 100 µAp-p, and the frequency thereof is limited to 1 MHz. Thus, in the embodiment of the invention, in order to measure a voltage by flowing a sinusoidal current of 100 µAp-p at 500 kHz to a human body, a sinusoidal voltage is generated and then converted into a current. When a sinusoidal voltage with a low frequency of 500 kHz is generated by a passive element, the passive element occupies a large area, and thus a sine wave is generated using a direct digital synthesizer (DDS) scheme using a digital logic, a DAC and an LPF. Since the DDS scheme uses a lookup table, values that are inputted to the DAC may be considered to have been digitally filtered in advance. Accordingly, a neat sine wave without noises may be obtained by low-pass filtering of only quantization noises occurring upon digital-to-analog changes of the values. In the embodiment of the invention, sampling is performed using a clock of 16 MHz, and a 5-bit lookup table and a 5-bit DAC are used. In order to reduce glitches occurring upon transition of each bit, the DAC uses a thermometer code rather than a binary code.

Figure 17:
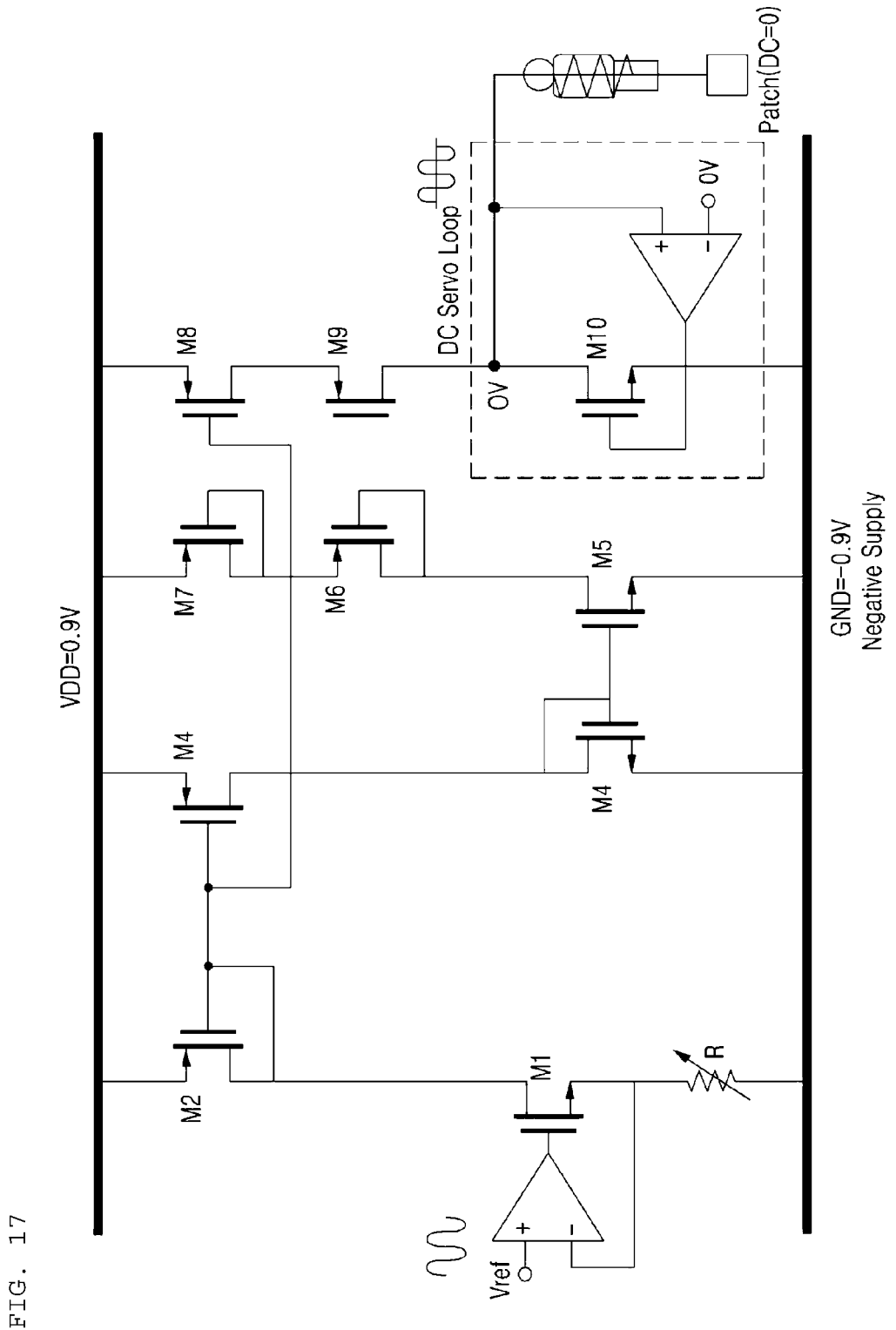
FIG. 17 illustrates an alternating current application circuit according to one embodiment of the invention.

FIG. 17 illustrates an alternating current application circuit according to one embodiment of the invention.

According to one embodiment of the invention, a sinusoidal voltage of 500 KHz generated in the DDS is converted into a current using a voltage-current converter. The maximum allowable DC current to be applied to a human body is specified as 10 μA by the medical regulations (IEC 60601-1). Thus, in order to comply with the regulations, a negative supply and a DC servo loop are used to generate an alternating current. In order to prevent a DC current from flowing in the human body, a patch voltage corresponding to a ground and an output voltage of the voltage-current converter should be equal. Accordingly, the circuit is driven using 0.9 V and −0.9 V and the median value of 0 V is designed as a common voltage of the output voltages. Further, since the DC current may flow into the human body due to a miss match, a change in a supply voltage, a change in a patch voltage, and the like, a DC servo loop is required so that an output node may always follow the patch voltage. The DC servo loop, which is a negative feedback loop using an op-amp with a high DC gain and a relatively low high-frequency gain, filters the DC current and flows only the sinusoidal current of 500 kHz into the human body.

Figure 18A:
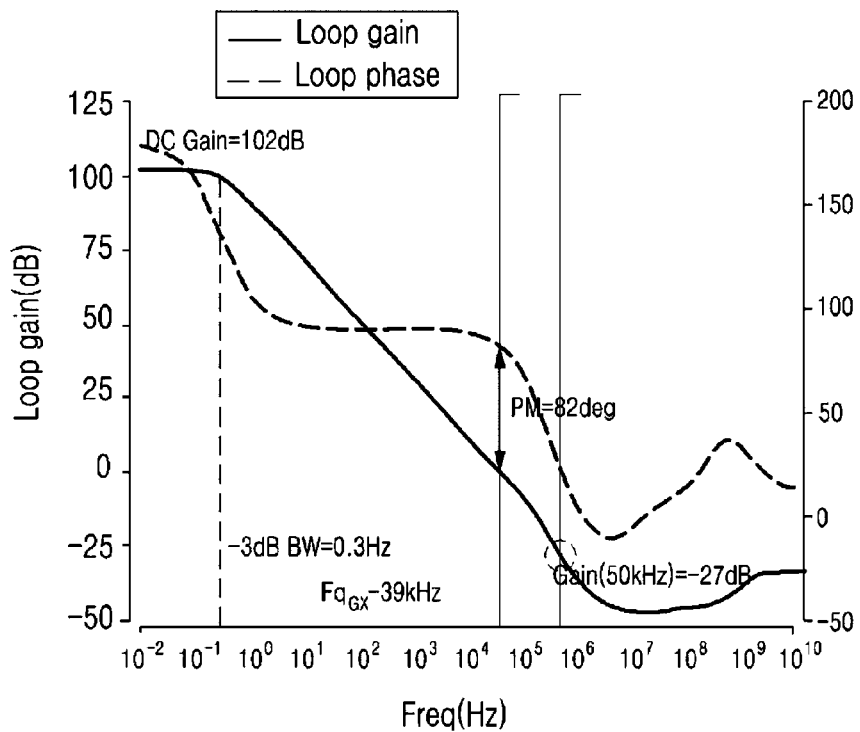
FIG. 18A illustrates a simulation result of an alternating current application circuit according to one embodiment of the invention.
Figure 18B:
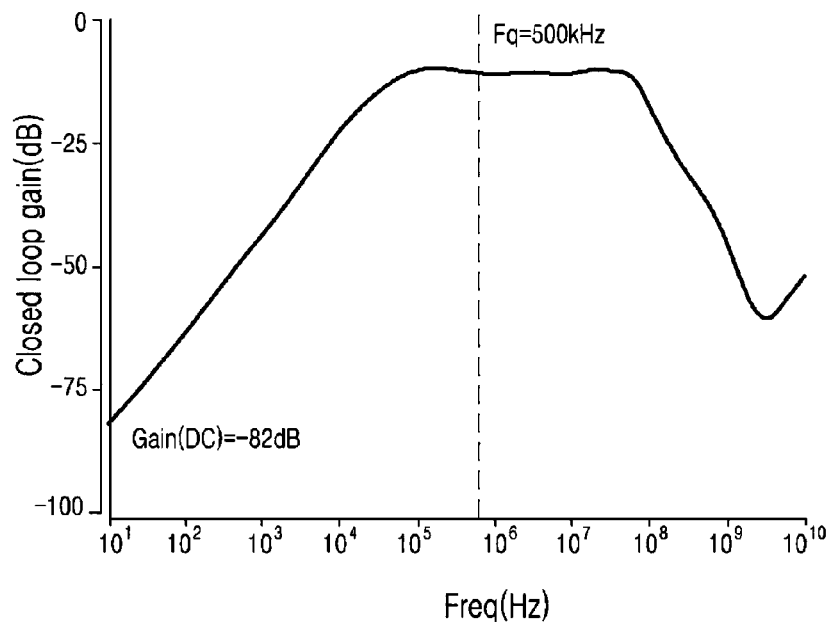
FIG. 18B illustrates a simulation result of an alternating current application circuit according to one embodiment of the invention.

FIGS. 18A and 18B illustrate a simulation result of an alternating current application circuit according to one embodiment of the invention.

FIG. 18A shows an open loop AC response of a DC servo loop, and FIG. 18B shows a closed loop AC response of the DC servo loop.

Figure 19:
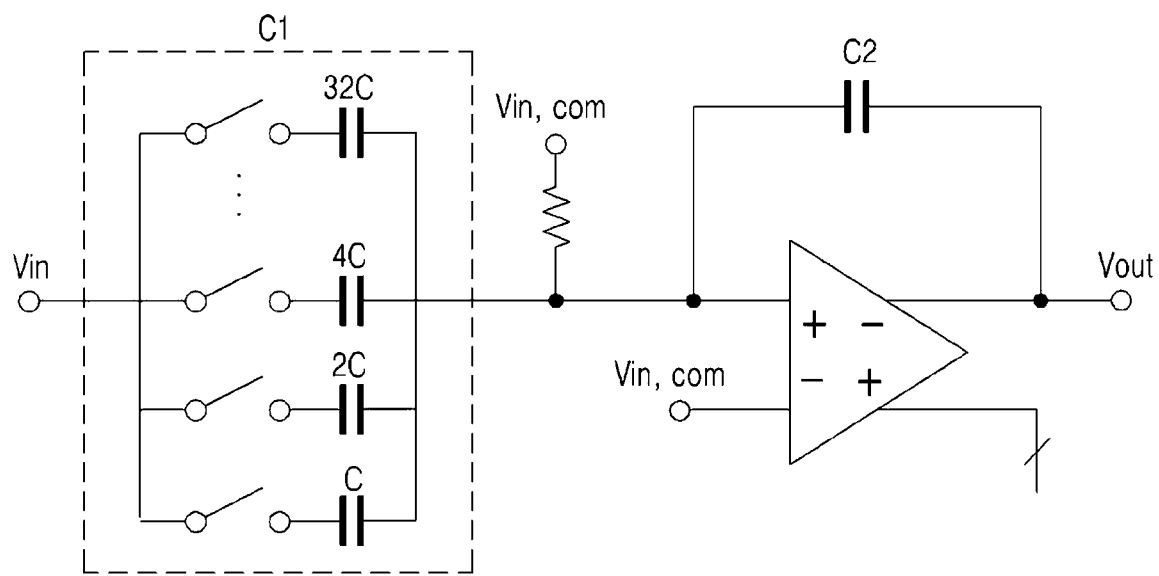
FIG. 19 illustrates a PGA circuit according to one embodiment of the invention.

FIG. 19 illustrates a PGA circuit according to one embodiment of the invention.

According to one embodiment of the invention, a value of a voltage for flowing a current into an electrode contacting an arterial wall is read to measure impedance. At this time, the approximate value of the contact impedance decreases from 300Ω to 100-200Ω as heat is applied. According to the medical regulations, the maximum alternating current that may be applied to a human body is 100 μAp-p, and thus a voltage of 30 mVp-p occurs at the contact due to the known contact impedance. The voltage is too low to be processed by an ADC with a full range of 1 V, and thus amplification of the voltage is required. Accordingly, a C2C PGA (Cap-to-Cap Programmable Gain Amplifier) is designed to have a maximum gain of 29 dB and to be digitally controlled with 6 bits. Since an input signal thereto does not have a bandwidth but has a single tone of 500 kHz, a gain needs to be guaranteed only at 500 kHz, so that there is no need to set a low 3 dB corner low. Thus, the low 3 dB corner is set to about 23 kHz. Further, since high frequency noises are not received at a high 3 dB corner, the high 3 dB corner is set to 1.23 MHz with a margin to ensure a gain designed at 500 kHz even for PVT variations.

Figure 20A:
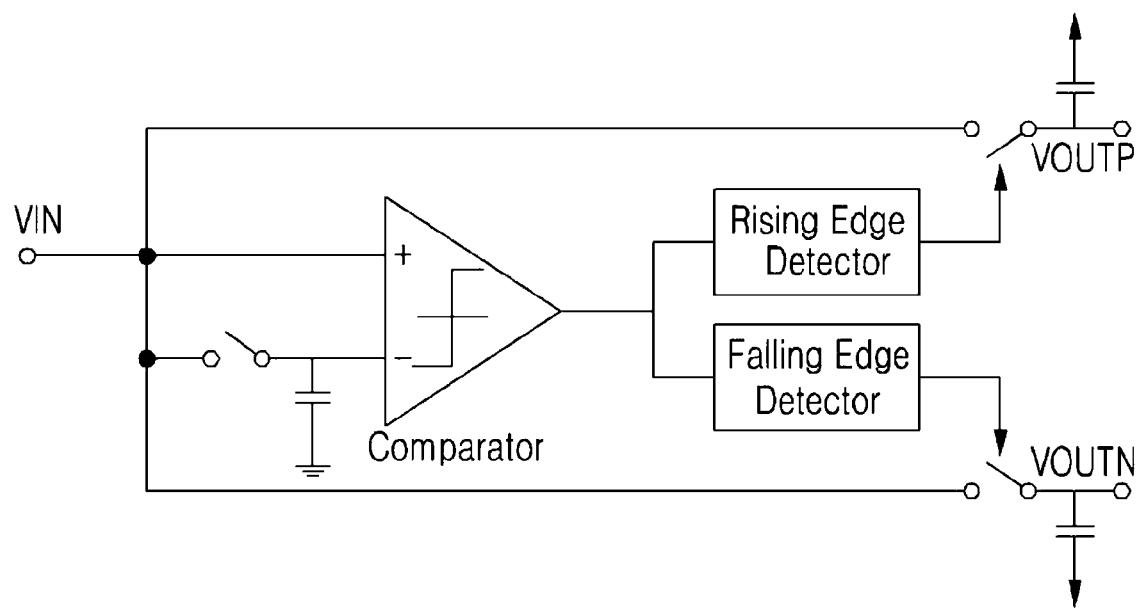
FIG. 20A illustrates a block diagram of a peak detector according to one embodiment of the invention.
Figure 20B:
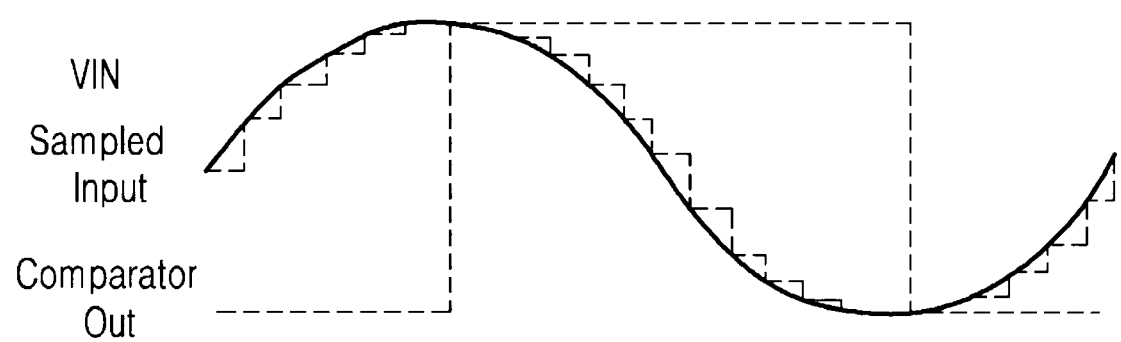
FIG. 20B illustrates a block diagram of a peak detector according to one embodiment of the invention.

FIGS. 20A and 20B illustrate a block diagram of a peak detector according to one embodiment of the invention.

FIG. 20A shows the structure of the peak-to-peak detector, and FIG. 20B shows the operation principle of the peak-to-peak detector.

Impedance consists of magnitude and phase. A renal artery denervation procedure only requires information on magnitude of the impedance, and thus only peak-to-peak information of an AC voltage is needed in order to measure the magnitude of the impedance. Accordingly, a peak-to-peak detector is needed in order for the ADC to read peak-to-peak information of the AC voltage amplified at the output of the C2C PGA. FIGS. 20A and 20B show the structure and operation principle of the peak-to-peak detector. An input sample-and-hold (S/H) circuit holds an input every clock cycle, and a comparator compares another input with the held input. The results of the comparator are inverted at the maximum and minimum, i.e., peaks, of the input, and thus the corresponding values are sampled to obtain the peak values.

Figure 21:
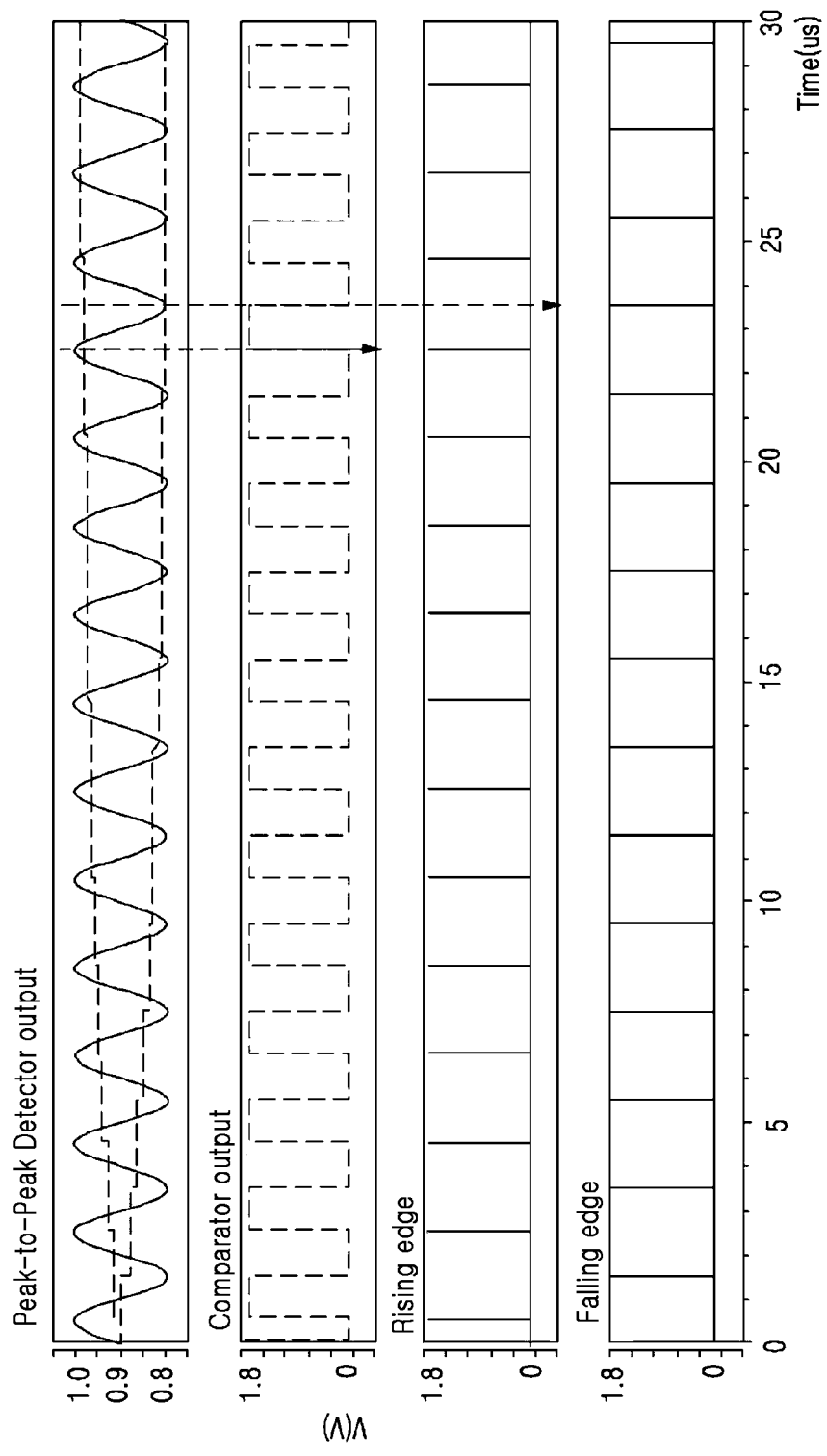
FIG. 21 illustrates a simulation result of a peak detector according to one embodiment of the invention.

FIG. 21 illustrates a simulation result of a peak detector according to one embodiment of the invention.

According to one embodiment of the invention, a peak value with a smaller error may be obtained as the speed of a sampling clock is higher, and thus 16 MHz, which is the fastest clock in the chip, is employed. Further, the clock is synchronized with an input signal in order to reduce gain errors.

Figure 22:
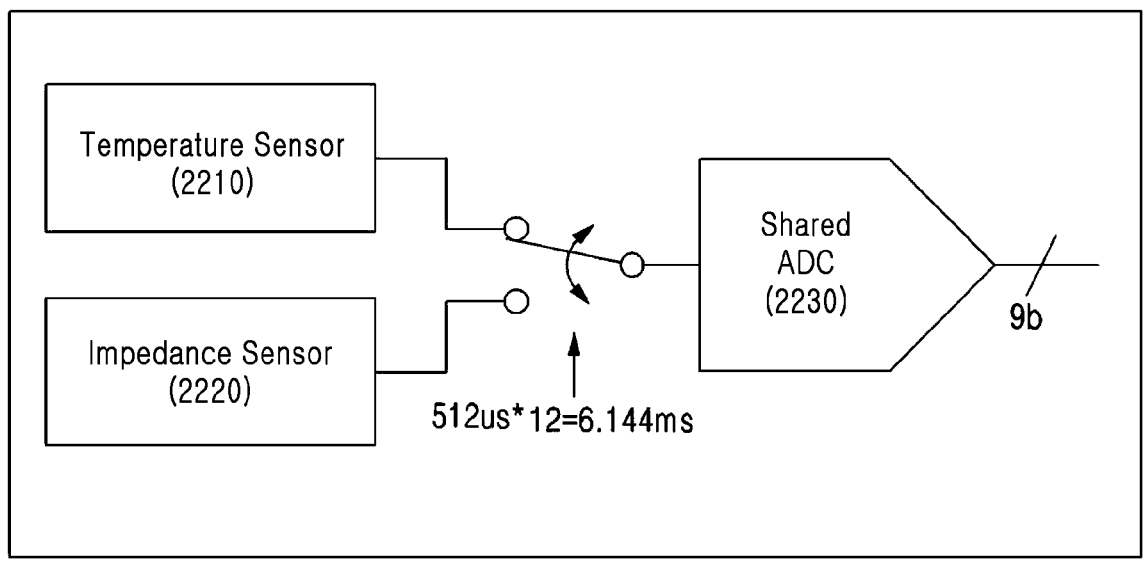
FIG. 22 illustrates a shared analog-to-digital converter (ADC) according to one embodiment of the invention.

FIG. 22 illustrates a shared analog-to-digital converter (ADC) according to one embodiment of the invention.

In order to transmit information on the temperature and impedance sensed by an IC to an external power generator using noise-resistant digital communication, an analog-to-digital converter (ADC) for digitally converting analog information is required. For example, in order to design an IC to be inserted into a kidney artery having a diameter of about 5 mm, the ADC should also be as small as possible. Thus, the present invention proposes a circuit for converting two types of information in real time by sharing one ADC, as shown in FIG. 22. The reason why the sharing of the ADC is possible is that the temperature and impedance changes are very slow compared to the operating speed of the ADC, and thus there is less information to lose even when the data sampling rate is slow.

The apparatus described above may be implemented as a hardware component, a software component, and/or a combination of hardware and software components. For example, the apparatus and components described in the embodiments may be implemented with one or more general or special purpose computers, such as a processor, a controller, an arithmetic logic unit (ALU), a digital signal processor, a microcomputer, a field programmable array (FPA), a programmable logic unit (PLU), a microprocessor, or any other device capable of executing and responding to instructions. The processing device may run an operating system (OS) and one or more software applications running on the operating system. Further, the processing device may also access, store, manipulate, process, and generate data in response to execution of the software. For ease of understanding, the processing device may be described as being used singly, but those skilled in the art will recognize that the processing device may include a plural number of and/or multiple types of processing elements. For example, the processing device may include a single or a plurality of processor(s) and a single controller. Other processing configurations, such as parallel processors, are also possible.

The software may comprise a computer program, codes, instructions, or a combination of one or more of the foregoing, and may configure the processing device to operate as desired, or may independently or collectively instruct the processing device. For interpretation by the processing device or for provision of instructions or data to the processing device, the software and/or data may be permanently or temporarily embodied in any type of machine, component, physical equipment, virtual equipment, computer storage media or equipment, or transmitted signal wave. The software may be distributed over a networked computer system and stored or executed in a distributed manner. The software and data may be stored on one or more computer-readable recording media.

The methods according to the embodiments may be implemented in the form of program instructions that may be executed by various computer means, and may be recorded in computer-readable media. The computer-readable media may include program instructions, data files, data structures, and the like, separately or in combination. The program instructions stored on the media may be specially designed and configured for the embodiments, or may also be known and available to those skilled in the computer software field. Examples of the computer-readable recording media include the following: magnetic media such as hard disks, floppy disks and magnetic tapes; optical media such as compact disk-read only memory (CD-ROM) and digital versatile disks (DVDs); magneto-optical media such as floptical disks; and hardware devices such as read-only memory (ROM), random access memory (RAM) and flash memory, which are specially configured to store and execute program instructions. Examples of the program instructions include not only machine language codes created by a compiler or the like, but also high-level language codes that can be executed by a computer using an interpreter or the like. The above hardware devices may be configured to operate as one or more software modules to perform the processes of the embodiments, and vice versa.

Although the present invention has been described above in terms of the limited embodiments and the drawings, those skilled in the art may make various modifications and changes from the above description. For example, proper results may be achieved even when the above-described techniques may be performed in different orders from those of the above-described methods, and/or the above-described elements such as systems, structures, devices, and circuits are coupled or combined differently from the described methods, or replaced or substituted by other elements or equivalents.

Therefore, other implementations, other embodiments, and equivalents of the following claims will fall within the scope of the claims.

What is claimed is:

1. A multi-electrode renal denervation system, comprising: a power generator configured to sequentially transmit control data for adjusting temperature of a plurality of electrodes through a single wire at predetermined time intervals using a time division communication scheme; and a catheter configured to transmit information measured by using an integrated circuit (IC) disposed within each of the plurality of electrodes to the power generator, wherein the plurality of electrodes are disposed in the catheter, and the IC is controlled by the control data received from the power generator, wherein the IC comprises a regulator configured to generate and supply a plurality of voltages required for respective blocks in the IC, using a supply voltage supplied from the power generator.

2. The system of claim 1, wherein the IC is connected to the power generator using a VDD line for supplying the supply voltage, a GND line, and a data line for data communication.

3. The system of claim 1, wherein the control data are in the form of packets transmitted from a micro controller unit (MCU) in the power generator, and the packets have predetermined ID data, and
wherein the ID data indicate that the control data are transmitted to a specific IC corresponding to a predetermined ID, among the ICs disposed within the plurality of electrodes.

4. The system of claim 3, wherein the specific IC receiving the control data transmits the information measured by using the IC to the power generator in a next time interval, after receiving the control data.

5. The system of claim 1, wherein the IC further comprises:
a communication unit configured to receive the control data from the power generator and to digitize the measured information, wherein the information is measured using a temperature sensor and an impedance sensor, and transmit the digitized information to the power generator through the single wire;
the temperature sensor configured to measure temperature using a temperature proportional current in a bandgap reference circuit;
the impedance sensor configured to measure impedance by applying a predetermined current and sensing an absolute value of a voltage change;
a shared analog-to-digital converter (ADC) configured to digitize the information measured by the temperature sensor and the impedance sensor; and
a heater configured to adjust the temperature by controlling power consumption using the control data received from the power generator.

6. The system of claim 5, wherein the heater converts the control data received from the power generator into PWM pulses through a PWM pulse generation circuit, and controls a plurality of MOSFET switches in parallel using the PWM pulses through a driver circuit, thereby controlling power consumption of resistance of the heater.

7. The system of claim 6, wherein the electrodes are configured to directly transfer heat to a blood vessel wall by controlling the power consumption of the resistance of the heater.

8. The system of claim 5, wherein the impedance sensor comprises:
a digital sine wave generator configured to generate a sine wave voltage using a DDS (Direct Digital Synthesizer) scheme;
an alternating current application circuit configured to convert the generated sine wave voltage into a current and apply an alternating current to the electrodes;
a programmable gain amplifier (PGA) configured to amplify an AC voltage caused by the alternating current applied to the electrodes to measure the impedance; and
a peak detector configured to detect peak-to-peak information of the amplified AC voltage.

9. The system of claim 5, wherein the shared ADC uses one shared ADC to convert two types of information measured by the temperature sensor and the impedance sensor in real time.

10. A method for driving a multi-electrode renal denervation system, comprising the steps of: transmitting control data from a power generator for adjusting temperature of a plurality of electrodes; and transmitting information from a catheter that has been measured by using an integrated circuit (IC) disposed within each of the plurality of electrodes to the power generator, wherein the plurality of electrodes are disposed in the catheter, and the IC is controlled by the control data received from the power generator, wherein the control data are sequentially transmitted through a single wire at predetermined time intervals using a time division communication scheme, and wherein the step of transmitting measured information by using the IC to the power generator comprises the step of: providing a regulator that generates and supplies a plurality of voltages required for respective blocks in the IC, using a supply voltage supplied from the power generator.

11. The method of claim 10, wherein in the step of transmitting the control data, frequency and phase synchronization is performed between a micro controller unit (MCU) in the power generator and the ICs disposed within the plurality of electrodes, before the control data are transmitted; and a specific IC receiving the control data transmits the information measured by using the IC to the power generator in a next time interval, after receiving the control data.

12. The method of claim 10, wherein the step of transmitting the measured information by using the IC to the power generator further comprises the steps of: measuring temperature by sensing a temperature proportional current in a bandgap reference circuit of a temperature sensor; measuring impedance by an impedance sensor applying a predetermined current and sensing an absolute value of a voltage change; using a shared analog-to-digital converter (ADC) to digitize information measured by the temperature sensor and the impedance sensor; transmitting the digitized information to the power generator through the single wire; and adjusting the temperature by controlling power consumption of a heater using the control data received from the power generator according to the information measured by the temperature sensor and the impedance sensor.

13. The method of claim 12, wherein in the step of measuring the temperature, an amount of a supply current of the heater is increased when the measured temperature is lower than a target temperature, and decreased when the measured temperature is higher than the target temperature.

14. The method of claim 12, wherein in the step of measuring the impedance, a sine wave voltage is generated using a DDS (Direct Digital Synthesizer) scheme; the generated sine wave voltage is converted into a current and an alternating current is applied to the electrodes; and an AC voltage caused by the alternating current applied to the electrodes to measure the impedance is amplified to detect peak-to-peak information of the amplified AC voltage.

15. The method of claim 12, wherein in the step of digitizing the information measured by the temperature sensor and the impedance sensor, one shared ADC is used to convert two types of information measured by the temperature sensor and the impedance sensor in real time.

16. The method of claim 12, wherein in the step of adjusting the temperature, the control data received from the power generator are converted into PWM pulses through a PWM pulse generation circuit; and a plurality of MOSFET switches are controlled in parallel using the PWM pulses through a driver circuit, thereby controlling power consumption of resistance of the heater.

17. The method of claim 16, wherein the electrodes are configured to directly transfer heat to a blood vessel wall by controlling the power consumption of the resistance.

* * * * *